(12) United States Patent
Lee et al.

(10) Patent No.: US 11,442,069 B2
(45) Date of Patent: Sep. 13, 2022

(54) METHOD OF DIAGNOSING CANCER AND DIAGNOSIS KIT USING MEASUREMENT OF NK CELL ACTIVITY

(75) Inventors: Jae Myun Lee, Seoul (KR); Joo Chun Yoon, Seoul (KR); Sang Woo Park, Seoul (KR); Jong Sun Kim, Seoul (KR)

(73) Assignee: ATGEN CO. LTD., Gyeonggi-Do (KR)

( * ) Notice: Subject to any disclaimer, the term of this patent is extended or adjusted under 35 U.S.C. 154(b) by 0 days.

(21) Appl. No.: 13/985,301

(22) PCT Filed: Feb. 10, 2012

(86) PCT No.: PCT/IB2012/000259
§ 371 (c)(1),
(2), (4) Date: Sep. 23, 2013

(87) PCT Pub. No.: WO2012/110878
PCT Pub. Date: Aug. 23, 2012

(65) Prior Publication Data
US 2014/0017713 A1 Jan. 16, 2014

(30) Foreign Application Priority Data

Feb. 14, 2011 (KR) .......................... 10-2011-0012983

(51) Int. Cl.
| | |
|---|---|
| G01N 33/68 | (2006.01) |
| C07K 14/55 | (2006.01) |
| C07K 14/54 | (2006.01) |
| C07K 14/47 | (2006.01) |
| G01N 33/574 | (2006.01) |

(52) U.S. Cl.
CPC ......... *G01N 33/6866* (2013.01); *C07K 14/47* (2013.01); *C07K 14/54* (2013.01); *C07K 14/5434* (2013.01); *C07K 14/5443* (2013.01); *C07K 14/55* (2013.01); *G01N 33/574* (2013.01); *C07K 2319/00* (2013.01); *C07K 2319/21* (2013.01); *G01N 2800/54* (2013.01)

(58) Field of Classification Search
CPC .............. G01N 33/6863; G01N 33/48; G01N 33/6866; G01N 33/56972; G01N 33/5047
See application file for complete search history.

(56) References Cited

U.S. PATENT DOCUMENTS

| | | | | |
|---|---|---|---|---|
| 5,744,132 A | * | 4/1998 | Warne | A61K 47/26 |
| | | | | 424/85.2 |
| 7,781,210 B2 | | 8/2010 | Tsuchiyama et al. | |
| 2005/0203010 A1 | | 9/2005 | Kim | |
| 2007/0110713 A1 | | 5/2007 | Paul | |
| 2010/0136052 A1 | | 6/2010 | Wolschek et al. | |
| 2010/0190155 A1 | * | 7/2010 | Norin | G01N 33/56972 |
| | | | | 435/6.1 |

FOREIGN PATENT DOCUMENTS

| | | | |
|---|---|---|---|
| JP | 2004-305095 A | 11/2004 | |
| JP | 2006115826 A | 6/2005 | |
| JP | 2006115826 A | 5/2006 | |
| JP | 2007-501618 A | 2/2007 | |
| JP | 2007-513072 A | 5/2007 | |
| JP | 2010515709 A | 5/2010 | |
| KR | 10-1989-0009978 | 8/1989 | |
| KR | 10-0506766 | 8/2005 | |
| KR | 10-0565764 | 3/2006 | |
| TW | 201245718 A | 11/2012 | |
| TW | 201741670 A | 12/2017 | |
| WO | WO03082206 A2 | 10/2003 | |
| WO | 2005/108423 A1 | 11/2005 | |
| WO | WO 2006110577 A2 * | 10/2006 | ........... A61K 38/168 |

OTHER PUBLICATIONS

Bermudez et al. Interleukin-12-Stimulated Natural Killer Cells Can Activate Human Macrophages To Inhibit Growth of *Mycobacterium avium*. Infection and Immunity. 1995. 63 (10):4099-4104.*
De Sanctis et al. Secretion of cytokines by natural killer cells primed with interleukin-2 and stimulated with different lipoproteins. Immunology. 1997; 90: 5526-533.*
Chan et al. Induction of Interferon γ Production by Natural Killer Cell Stimulatory Factor: Characterization of the Responder Cells and Synergy with Other Inducers. Journal of Experimental Medicine. 1991; 173:869-879.*
Haicheur et al. Cytokines and soluble cytokine receptor induction after IL-12 administration in cancer patients. Clinical Experimental Immunology. 2000; 119:28-37.*
Weidmann et al. Rapid cytokine release in cancer patients treated with interleukin-2. Journal of Immunotherapy. Aug. 1992; 12(2):123-31.*
Uno et al. Differential interleukin 12 responsiveness for interferon gamma production in advanced stages of cancer patients correlates with perfromance status. Clinical Cancer Research, 1998; 4:2425-2432.*
Pedraza-Sanchez et al. The immunostimulant RU41740 from Klebsiella pneumoniae activates human cells in whole blood to potentially stimulate innate and adaptive immune responses. International Immunopharmacology, 2006; 6:635-646.*
Wang et al. Interleukin-2 enhances the response of natural killer cells to interleukin-12 through up-regulation of the interleukin-12 receptor and STAT4. Blood. 2000; 95(10): 3183-3190.*
Schwartz and Conley. "Blood". Encyclopædia Britannica. Encyclopædia Britannica Online. Encyclopædia Britannica Inc., 2017. Web. Mar. 3, 2017,<https://www.britannica.com/science/blood-biochemistry>.*

(Continued)

*Primary Examiner* — Vanessa L. Ford
*Assistant Examiner* — Sandra Dillahunt
(74) *Attorney, Agent, or Firm* — Nixon Peabody LLP; David S. Resnick; Nicole D. Kling

(57) ABSTRACT

Provided are a method for diagnosing cancer, a diagnosis kit and compositions useful for measurement of NK cell activity. The incidence of cancer may be diagnosed by monitoring changes in the in vivo immune system through measurement of NK cell activity in blood. Thus, the incidence of cancer may be readily predicted as described herein using a blood sample from a subject.

33 Claims, 9 Drawing Sheets

Specification includes a Sequence Listing.

(56) References Cited

OTHER PUBLICATIONS

Uno et al. Differential interleukin 12 responsiveness for interferon gamma production in advanced stages of cancer patients correlates with performance status. Clinical Cancer Research, 1998; 4:2425-2432.*

Claus et al. Evaluation of Human Natural Killer Cell Activities in Whole Blood. Current Protocols in Immunology, Nov. 2010; 7.39. 1-17.*

Wang et al. IL-2 enhances the response of natural killer cells to interleukin-12 through up-regulation of the interleukin-12 receptor and STAT4. Blood. 2000; 95(10): 3183-3190.*

Zhang et al. The effect of the reconstitution medium on aggregation of lyophilized recombinant interleukin-2 and ribonuclease A. Pharmaceutical Research. 1996; 13(4): 643-646.*

Lee et al. Stabilizing peptide fusion for solving the stability and solubility problems of therapeutic proteins. Pharmaceutical Research, 2005; 22(10): 1735-1746.*

Schwartz and Conley. "Blood". Encyclopaedia Britannica. Encyclopaedia Britannica Online. Encyclopaedia Britannica Inc., 2017. Web. Mar. 3, 2017,<https://www.britannica.com/science/blood-biochemistry>. (Year: 2017).*

Uno et al. Differential interleukin 12 responsiveness for interferon gamma production in advanced stages of cancer patients correlates with performance status. Clinical Cancer Research, 1998; 4:2425-2432 (Year: 1998).*

Wang et al. IL-2 enhances the response of natural killer cells to interleukin-12 through up-regulation of the interleukin-12 receptor and STAT4. Blood. 2000; 95(10): 3183-3190 (Year: 2000).*

Zhang et al. The effect of the reconstitution medium on aggregation of lyophilized recombinant interleukin-2 and ribonuclease A. Pharmaceutical Research. 1996; 13(4): 643-646 (Year: 1996).*

Lee et al. Stabilizing peptide fusion for solving the stability and solubility problems of therapeutic proteins. Pharmaceutical Research, 2005; 22(10): 1735-1746 (Year: 2005).*

Bowie et al. (Science, 1990, 247:1306-1310) (Year: 1990).*

Lazar et al. Mol. Cell. Biol., 8:1247-1252,1988 (Year: 1988).*

Bork Genome Research, 2000,10:398-400 (Year: 2000).*

Burgess et al. (J. Cell Biol. 111:2129-2138,1990 (Year: 1990).*

Puren et al. (The Journal of Infectious Diseases, 1998; 178:1830-4 (Year: 1998).*

Riber et al. Co-incubation with Il-18 potentiates antigen-specific IFN-gamma response in a whole blood stimulation assay for measurement of cell-mediated immune responses in pigs experimentally with Lawsonia intracellularis. Vet. Immunol Immunopathol. Epub Sep. 21, 2010; 139(2-4):257-63. (Year: 2010).*

Denis et al. Clinical and Vaccine Immunology, 2007; 14(11):1483-1489 (Year: 2007).*

Carson et al. Journal of Experimental Medicine, 1994; 180: 1395-1403 (Year: 1994).*

Reddy, M. and Prabhakar, U. (2008). Whole Blood Ex vivo Stimulation Assay Development, Optimization and Validation. In Validation of Cell-Based Assays in the GLP Setting (eds U. Prabhakar and M. Kelley) (Year: 2008).*

Ziolkowska et al. Immunology Letters 73(2-3): 201; 2000 (Year: 2000).*

Geluk et al. Clinical and Vaccine Immunology, 2010; 17(6):993-1004 (Year: 2010).*

Lee et al., The Journal of Immunology, 167 (1): 497-504 (2001). "Both E6 and E7 oncoproteins of human papillomavirus 16 inhibit IL-18-induced I FN-gamma production in human peripheral blood mononuclear and NK cells."

Lingren et al., Experimental Cell Research, Avademic Press, 314(6): 849-858 (2011). "Impaired I FN-production after stimulation with bacterial components by natural kller cells from gastric cancer patients."

Parihar et al., Journal of Clinical Investigation, 110 (7): 983-992 (2002). "IL-12 enhances the natural killer cell cytokine response to Ab-coated tumor cells."

Tajima et al., Leukemia (Basingstoke) 10(3): 478-482 (1996). "Natural killer cell activity and cytokine production as prognostic factors in adult acute leukemia."

Takeuchi et al., The American Journal of Gastroenterology, 96(2): 574-578 (2001). "Prognostic significance of natural killer cell activity in patients with gastric carcinoma: a multivariate analysis."

Nguyen, Khuong B. et al., The Journal of Immunology 169:4279-4287 (2002). "Coordinated and Distinct Roles for IFN-αβ, IL-12, and IL-15 Regulation of NK Cell Responses to Viral Infection."

Pyun et al., Korea Research Institute of Bioscience and Biotechnology (1994). "Studies on the development of screening techniques for cell growth regulating factors: Development of screening systems for immune cell growth regulators and investigation for their actions."

Vester, Bettina et al., Infection and Immunity 67(9):3155-3159 (Jun. 1999). "Early Gene Expression of NK Cell-Activating Chemokines in Mice Resistant to Leishmania major."

Kane et al., Clinical and Diagnostic Laboratory Immunology, 3(3):295-300 (1996). "Determination of natural killer cell function by flow cytometry."

Mian et al., Journal of Leukocyte Biology, 83(3):774-784 (2008). "Impairment of human NK cell cytotoxic activity and cytokine release by cigarette smoke."

Takeda et al., Clinical and Experimental Immunology, 146:109-115 (2006). "Interleukin-12 is involved in the enhancement of human natural killer cell activity by Lactobacillus casei Shirota."

NCBI PDB: 3DUH_A, GI:197107463, "Chain A, Structure of Interleukin-23", (2012).

NCBI GenBank: CAP05189.1, GI: 164512501, "interleukin 2, partial [synthetic construct]" (2008).

NCBI PDB: 1F45_B, GI: 14719641, "Chain B, Human Interleukin-12", (2012).

NCBI GenBank: CAA86100, GI: 995657, "interleukin-15, partial [Homo sapiens]", (2006).

NCBI PDB: PDB: 1J0S_A, GI: 39654070,"Chain A, Solution Structure Of The Human Interleukin-18", (2012).

NCBI GenBank: AB590700.1, GI: 307685848, "Synthetic construct DNA, clone: pFN21AE1812, Homo sapiens IL 12B gene for interleukin 12B, without stop codon, in Flexi system", (2010).

NCBI GenBank: AY523040.1, GI: 42495055, "Homo sapiens interleukin-2 mRNA, complete cds", (2004).

NCBI GenBank: AY191828.1, GI: 27729523, "Synthetic construct evolved IL-12 p35 precursor, mRNA, partial cds", (2003).

NCBI GenBank: X94222.1, GI: 1495459, "H. sapiens mRNA for interleukin-15 (cell line NCIH69)", (1996).

NCBI GenBank: AF454397.1, GI: 17981381, "Synthetic construct EGF-IL18 fusion protein mRNA, complete cds", (2005).

Claus et al., "Evaluation of Human Natural Killer Cell Activities in Whole Blood", Current Protocols in Immunology Chapter 7:Unit 7.39(Supplement 91) (2010).

Claus et al., "Comprehensive analysis of NK cell function in whole blood samples", Journal of Immunological Methods 341:154-164 (2009).

Fehniger et al., "Differential Cytokine and Chemokine Gene Expression by Human NK Cells Following Activation with IL-18 or IL-15 in Combination with IL-12: Implications for the Innate Immune Response", The Journal of Immunology 162:4511-4520 (1999).

Kim et al., "Expression of human interferon alpha-1 with enhanced stability via the tagging system of a stabilizing peptide", Protein Expression and Purification 63:140-146 (2009).

Mendes et al. "Flow cytometric visualisation of cytokine production by CD3-CD56+ NK cells and CD3+ CD56+ NK-T cells in whole blood." Cytometry 39(1):72-78 (2000).

Seidel et al., "Increased CD56+ natural killer cells and related cytokines in major depression." Clinical immunology and immunopathology 78(1):83-85 (1996).

Jung et al., "IFN-γ is only partially restored by co-stimulation with IL-12, IL-2, IL-15, IL-18 or engagement of CD28", Clinical and Experimental Allergy 29(2):207-216 (1999).

Zamai et al., "NK Cells and Cancer", The Journal of Immunology 178(7):4011-4016 (2007).

Harandi et al., "Interleukin-12 (IL-12) and IL-18 Are Important in Innate Defense against Genital Herpes Simplex Virus Type 2

(56) References Cited

OTHER PUBLICATIONS

Infection in Mice but Are Not Required for the Development of Acquired Gamma Interferon-Mediated Protective Immunity", Journal of Virology 75(14):6705-6709 (2001).

Hodge et al., "IL-2 and IL-12 Alter NK Cell Responsiveness to IFN-γ-Inducible Protein 10 by Down-Regulating CXCR3 Expression", The Journal of Immunology 168:6090-6098 (2002).

Lin et al., "Effect of Interleukin (IL)-12 and IL-15 on Activated Natural Killer (ANK) and Antibody-Dependent Cellular Cytotoxicity (ADCC) in HIV Infection", Journal of Clinical Immunology 18(5):335-345 (1998).

Weigent et al., "Interleukin 2 Enhances Natural Killer Cell Activity Through Induction of Gamma Interferon", Infection and Immunity 41(3):992-997 (1983).

Yu et al., "IL-2 Activation of NK Cells: Involvement of MKK1/2/ERK But Not p38 Kinase Pathway", The Journal of Immunology 164:6244-6251 (2000).

\* cited by examiner

A

B

C

D

ID

METHOD OF DIAGNOSING CANCER AND DIAGNOSIS KIT USING MEASUREMENT OF NK CELL ACTIVITY

CROSS-REFERENCE TO RELATED APPLICATIONS

This application is a 35 U.S.C. § 371 National Phase Entry Application of International Application No. PCT/IB2012/000259 filed Feb. 10, 2012, which designates the U.S., and which claims priority to and the benefit of Korean Patent Application No. 10-2011-0012983, filed on Feb. 14, 2011, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 12, 2013, is named 201371-078970_SequenceListing.txt and is 22,775 bytes in size.

BACKGROUND

1. Field of the Invention

The present invention relates to a method for diagnosing cancer and a diagnosis kit using measurement of NK cell activity.

2. Discussion of Related Art

It is known that natural killer (NK) cells take part in innate immunity to remove pathogens and cancer cells, and secrete interferon-gamma (IFN-γ), tumor necrosis factor-alpha (TNF-α), macrophage inflammatory protein-1β (MIP-1β) and other molecules to mediate the adaptive immunity. When NK cells encounter other cells, the NK cells have a mechanism in which, when MHC Class 1 is not present as in cancer cells, or a shape of MHC Class is abnormal as in cells infected with viruses, their major histocompatibility complexes (MHCs) send signals into the NK cells to attack these abnormal cells through their molecular actions. However, since NK cells have been reported to have defects in functions and differentiation capacities in various kinds of cancers, NK cell activity is closely associated with the survival of cancer cells. Therefore, research is being widely conducted to increase the number, or activity of NK cells for cancer immunotherapy.

Meanwhile, methods of diagnosing cancer have mainly included finding the presence of cancer from graphic images obtained using computed tomography (CT), magnetic resonance imaging (MRI) or X rays. However, since these tests are generally conducted only when a patient has a strong need to undergo the tests due to pain or inconvenience, and are performed only in certain tissues, the presence of cancer may be overlooked. A method of determining the risk of cancer using a blood test has been developed, but its use as a method of diagnosing cancer is limited. This is because a patient may appear to be positive for cancer when an etiological factor is present in the corresponding organ rather than cancer, since the method is conducted using blood tumor markers, e.g. for prostate cancer, colon cancer, ovarian cancer, pancreatic cancer or liver cancer. There have also been attempts to diagnose cancer using antibodies, but such attempts are limited to certain types of cancer.

Accordingly, there continues to be a need for new methods for diagnosing cancers of various types.

SUMMARY OF THE INVENTION

It is therefore an object of the invention to provide a method that can be used in the diagnosis and evaluation of cancer, as well as kits and reagents useful in such a method.

As an aspect of the invention, there is provided a method of measuring NK cell activity, the method comprising stimulating NK cells in a blood sample thereby artificially activating the NK cells to generate NK cell-secreting cytokines and measuring an amount of the NK cell-secreting cytokines in the blood sample.

In certain non-limiting embodiments, the blood sample may be a sample of whole blood, peripheral blood mononuclear cells (PBMCs) or NK cells.

In further embodiments, the stimulation of the NK cells may be performed by incubating the blood sample with at least one stimulating cytokine including interleukin 2, interleukin 12, interleukin 15 and interleukin 18, or combinations thereof, or by incubating the blood sample with lipopolysaccharides (LPSs) or polyinosinic:polycytidylic acid (poly I:C).

The NK cell-secreting cytokines may, in certain embodiments, comprise interferon-gamma (IFN-γ), tumor necrosis factor-alpha (TNF-α) or macrophage inflammatory protein-1β (MIP-1β).

In further non-limiting embodiments of the method, macrophage inflammatory protein-1β (MIP-1β) can be used as control group for comparing activation of NK cells with that of a normal person.

In addition, the method may in certain embodiments be carried out using at least one stimulating cytokine fused to a stabilizing peptide. For example, yet without wishing to be limiting, the stabilizing peptide may be a C-terminal acidic tail domain peptide of a synuclein family. In such embodiments, the stabilizing peptide may comprise amino acid residues 103-115 (SEQ ID NO: 22), amino acid residues 114-126 (SEQ ID NO: 23), amino acid residues 119-140 (SEQ ID NO: 24) or amino acid residues 130-140 (SEQ ID NO: 25) of the C-terminal acidic tail domain of α-synuclein, amino acid residues 85-134 of the C-terminal acidic tail domain of β-synuclein (SEQ ID NO: 27), amino acid residues 96-127 of the C-terminal acidic tail domain of γ-synuclein (SEQ ID NO: 29), or amino acid residues 96-127 of the C-terminal acidic tail domain of synoretin (SEQ ID NO: 29).

In further embodiments, the step of stimulating NK cells in a blood sample thereby artificially activating the NK cells to generate NK cell-secreting cytokines is performed in a medium containing a carrier protein, for example a serum albumin protein.

The method as described is particularly useful for detecting the incidence or relapse of cancer. In such embodiments, a decrease in the amount of the NK cell-secreting cytokines in a subject, as compared to levels in normal individuals, is an indicator of cancer incidence or relapse.

As a further aspect of the invention there is provided a kit for measuring NK cell activity. The kit will comprise an agent for stimulating the NK cells in a blood sample thereby artificially activating the NK cells to generate NK cell-secreting cytokines. In addition, the kit may be useful for carrying out the method as described above, including for detecting the incidence or relapse of cancer.

In further non-limiting embodiments of the described kit, the NK cell-secreting cytokine may be interferon-gamma (IFN-γ) or tumor necrosis factor-alpha (TNF-α).

In a further embodiment, the agent for stimulating the NK cells in the blood sample and artificially activating the NK cells to generate the NK cell-secreting cytokines may comprise at least one stimulating cytokine, LPS or poly I:C, the at least one stimulating cytokine including one or more of interleukin 2, interleukin 12, interleukin 15 and interleukin 18.

The described kit may also comprise, in certain embodiments, one or more of the following: anti-INF-γ antibody, an anti-TNF-α antibody, and an anti-MIP-1β antibody. Without wishing to be limiting in any way, the kit may also further comprise instructions for comparing the amount of the NK cell-secreting cytokines in a subject to levels in normal individuals, wherein a decrease in the level of the NK cell-secreting cytokines in the subject is an indicator of cancer incidence or relapse.

As a further aspect of the invention, there is provided a fusion protein comprising a cytokine bound to a C-terminal acidic tail domain peptide of a synuclein family, the cytokine being either interleukin 2, interleukin 12, interleukin 15 or interleukin 18.

In certain non-limiting embodiments of the described fusion protein, the C-terminal acidic tail domain peptide of the synuclein family may comprise amino acid residues 103-115 (SEQ ID NO: 22), amino acid residues 114-126 (SEQ ID NO: 23), amino acid residues 119-140 (SEQ ID NO: 24) or amino acid residues 130-140 (SEQ ID NO: 25) of the C-terminal acidic tail domain of α-synuclein, amino acid residues 85-134 of the C-terminal acidic tail domain of β-synuclein (SEQ ID NO: 27), amino acid residues 96-127 of the C-terminal acidic tail domain of γ-synuclein (SEQ ID NO: 29), or amino acid residues 96-127 of the C-terminal acidic tail domain of synoretin (SEQ ID NO: 29).

Compositions comprising the above-described fusion protein are also provided.

In addition, cancer diagnosis kits comprising either the above-described fusion proteins or the above-described compositions are also provided herein.

The cancer diagnosis kit, as described above, may in certain non-limiting embodiments also include at least one antibody among the following: an anti-INF-γ antibody, an anti-TNF-α antibody and an anti-MIP-1β antibody.

There is also provided herein a polypeptide comprising an amino acid sequence having at least 80% identity to an amino acid sequence of SEQ ID NO: 2, SEQ ID NO: 4, SEQ ID NO: 6, SEQ ID NO: 8, or SEQ ID NO: 10. Without wishing to be limiting, the polypeptide may have a higher percent identity, including 81%, 82%, 83%, 84%, 85%, 86%, 87%, 88%, 89%, 90%, 91%, 92%, 93%, 94%, 95%, 96%, 97%, 98%, 99% or 100% identity to the sequences of SEQ ID NO: 2, SEQ ID NO: 4, SEQ ID NO: 6, SEQ ID NO: 8, and SEQ ID NO: 10.

Oligonucleotides encoding the above-described fusion proteins and polypeptides are also provided. For instance, an oligonucleotide is provided comprising a nucleic acid sequence with at least 80% identity to a nucleic acid sequence of SEQ ID NO: 1, SEQ ID NO: 3, SEQ ID NO: 5, SEQ ID NO: 7, or SEQ ID NO: 9, or the complement thereof. Such oligonucleotides may, without limitation, have a higher percent identity, including 81%, 82%, 83%, 84%, 85%, 86%, 87%, 88%, 89%, 90%, 91%, 92%, 93%, 94%, 95%, 96%, 97%, 98%, 99% or 100% identity to the sequences of SEQ ID NO: 1, SEQ ID NO: 3, SEQ ID NO: 5, SEQ ID NO: 7, or SEQ ID NO: 9, or the complementary sequences thereof.

Vectors comprising the oligonucleotides described above are also provided, as are host cells comprising such vectors or oligonucleotides.

BRIEF DESCRIPTION OF THE DRAWINGS

The above and other objects, features and advantages of the present invention will become more apparent to those of ordinary skill in the art by describing in detail exemplary embodiments thereof with reference to the drawings, in which.

DETAILED DESCRIPTION

Figure 1:
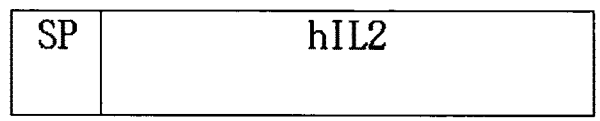
FIG. 1 is a schematic view showing the fusion products of an SP peptide fused either with the N terminus or C terminus of a cytokine, including hIL2, hIL12, hIL15 and hIL18.
Figure 1:
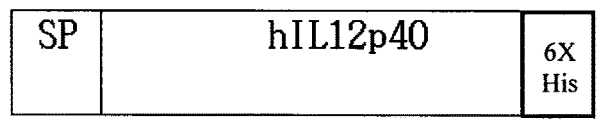
Figure 1:
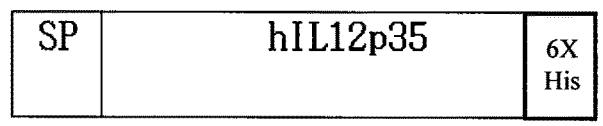
Figure 1:
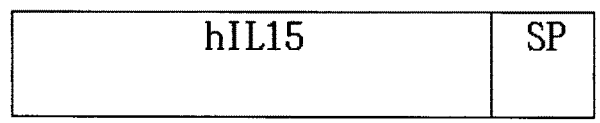
Figure 1:
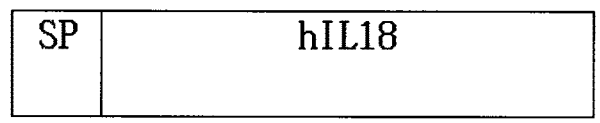
Figure 2:
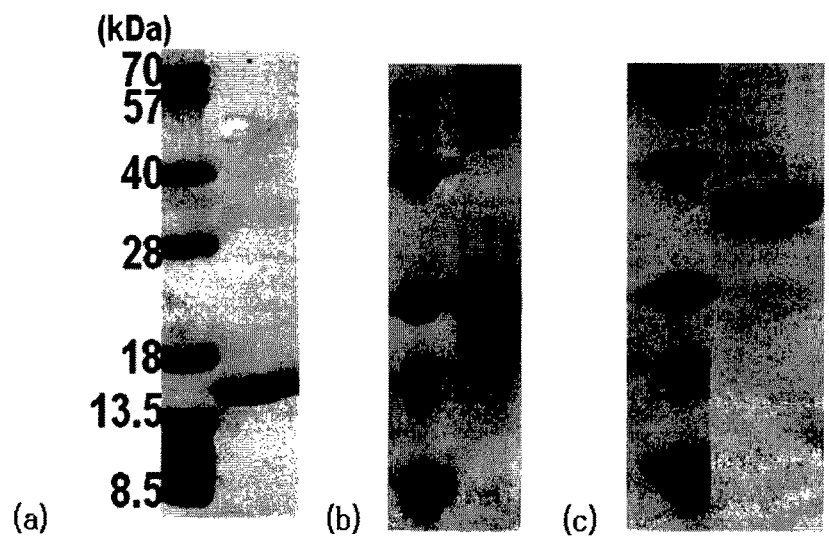
FIGS. 2A-2C are photographs showing the electrophoresis results of the purified SP fusion proteins (SP-hIL2 protein (ATGen, Cat #ATGK04) is shown in FIG. 2A; IL15-SP protein (ATGen, Cat #ATGK06) is shown in FIG. 2B; and SP-IL18 protein (ATGen, Cat #ATGK07) is shown in FIG. 2C).

The present invention is directed to a method, kit, and reagents for diagnosing cancer incidence using the interrelationship of cancer and NK cells.

For this purpose, there is provided a method of measuring NK cell activity comprising stimulating NK cells in a blood sample thereby artificially activating the NK cells to generate NK cell-secreting cytokines, and measuring an amount of the NK cell-secreting cytokines in the blood sample.

The present inventors have found that, based on the an observation that NK cell activity is reduced in cancer patients, the incidence of cancer may be primarily screened by measuring NK cell activity. The method described herein is capable of determining whether or not the NK cells function normally by giving an artificial stimulus to the NK cells, and measuring an activation level of the NK cells by detecting changes in the amount of NK cell-secreting cytokines present in a blood sample, which differs from other methods which simply measure the number of the NK cells or an amount of cytokines originally present in the blood sample. For example, in a conventional method of measuring an activation level of the NK cells, a $^{51}$Cr release assay has been used as a method of measuring the target-specific cytotoxicity. However, when the NK cell activity is measured in this manner, a radioactive isotope should be used, and measurement and analysis are difficult, complicated and costly. Therefore, the assay is unsuitable for use in primary cancer screening/testing methods which can simply diagnose the incidence of cancer. On the other hand, according to the present invention, since NK cell activity may be measured by stimulating the NK cells to generate NK cell-secreting cytokines and quantifying the generated NK cell-secreting cytokines, a subject in which NK cell activity is reduced may be advantageously screened as a subject suffering from cancer or at risk of suffering from cancer.

According to the present invention, the blood sample may include, but is not limited to, whole blood, peripheral blood mononuclear cells (PBMCs) and NK cells, which are taken from the subject. The PBMCs or NK cells may be used intact instead of the whole blood, but the use of the whole blood may be advantageous in certain embodiments due to simpler methodology and reduced costs.

Meanwhile, in the present invention, the term "subject" refers to a mammal that is suspected of suffering from cancer or having a relapse of cancer, or that wishes to determine the incidence or relapse of cancer.

The NK cells present in the blood sample are generally present in an inactivated state. According to the present invention, at least one cytokine, lipopolysaccharide (LPS) or polyinosinic:polycytidylic acid (poly I:C) may be used as an agent, also referred to herein as an agonist or activator, that serves to stimulate such NK cells in the blood sample and artificially activate the NK cells to generate NK cell-secreting cytokines. Here, the cytokine used for activating NK cells may be interleukin 2, interleukin 12, interleukin 15 and interleukin 18, or combinations thereof. The interleukin 2, the interleukin 12, the interleukin 15, the interleukin 18, the LPS or the poly I:C are widely known in the art to be stimulated to generate the NK cell-secreting cytokines. Therefore, according to one exemplary embodiment of the present invention, the stimulation of the NK cells may be performed by incubating the blood sample with the at least one cytokine, including interleukin 2, interleukin 12, interleukin 15 and/or interleukin 18, or by incubating the blood sample with LPS or poly I:C.

In one non-limiting embodiment, the stimulation of the NK cells may be performed by incubating the blood sample with Interleukin 2. Interleukin 2 is one of the cytokines secreted by the T cells, and is known to be associated with activation of the NK cells by T cells in an in vivo adaptive immune response. Also, the interleukin 2 is a cytokine that is generally widely used to activate the NK cells in vitro. Therefore, the stimulation of the NK cells may be performed by incubating the blood sample with the interleukin 2.

In another non-limiting embodiment, the stimulation of the NK cells may be performed by incubating the blood sample with Interleukin 2 and Interleukin 12. In case of cancer patients in early stage, the activity of T cells may be high even though the activity of NK cells is low. In contrast, in case of cancer patients in late stage, the activity of T cells as well as NK cells may be low. Interleukin 12 takes part in activating T cells as well as NK cells. Thus, if interleukin 12 with interleukin 2 is treated, cytokines secreted due to stimulation of T cells are added to the cytokine secreted from NK cells. Therefore, it is possible to evaluate total level of immunity as well as anticancer immunity of NK cells, and use this level as a marker representing degree of process of cancer or prognosis of cancer treatment. The interleukin 15 and the interleukin 18 are cytokines secreted by activated dendritic cells and macrophages, and induce activation and growth of the NK cells during an in vitro innate immune response. In particular, when the interleukin 12 is combined with the interleukin 15 or the interleukin 18, a relatively small amount of the interleukin 12 may be used to stimulate the secretion of the NK cell-secreting cytokines in the NK cells. Therefore, the stimulation of the NK cells may be effectively performed by incubating the blood sample with the interleukin 12 and the interleukin 15, or with the interleukin 12 and the interleukin 18.

According to the present invention, a numerical value of the NK cell-secreting cytokines is used as a measure to evaluate NK cell activity. In the present invention, "NK cell-secreting cytokines" refers to cytokines secreted from NK cells, in particular cytokines from activated NK cells by artificial stimulation. In one embodiment, the NK cell-secreting cytokines are at least one cytokine selected from the group of interferon-gamma (IFN-γ), tumor necrosis factor-alpha (TNF-α) and macrophage inflammatory protein-1β (MIP-1β). The interferon-γ is secreted by NK cells, dendritic cells, Tc cells, Th1 cells, and the like, and is known to be a cytokine that takes an important role in innate immunity and adaptive immunity for the control of cancer. Also, tumor necrosis factor-alpha (TNF-α) kills cancer cells and further take part in killing external intruder such as bacteria, inducing activation of T cells, and playing a role as a supplementary factor for producing antibody from B cells. Therefore, for example, when the numerical value of the interferon-γ or tumor necrosis factor-alpha is smaller than that of the interferon-γ or tumor necrosis factor-alpha from a normal person, this indicates that the NK cell activity for the control of cancer is problematic. Therefore, it is possible to determine NK cell activity by comparing an amount of the interferon-γ or tumor necrosis factor-alpha secreted from the artificially activated NK cells with an amount of the interferon-γ or tumor necrosis factor-alpha from the normal person.

Meanwhile, macrophage inflammatory protein-1β (MIP-1β) can be used as control group for comparing activation of NK cells. As shown in the following examples, the numerical value of macrophage inflammatory protein-1β (MIP-1β) is similarly high in both normal persons and cancer patients. Thus, macrophage inflammatory protein-1β (MIP-1β) can be used for analyzing the activity of NK cells in normal persons and cancer patients, or can be used as an control group for analysis using a cancer diagnosis kit.

Quantification of the NK cell-secreting cytokines may be performed by any methods known in the art, but the present invention is not limited thereto. For example, the quantification of the interferon-γ may be performed using an interferon-γ enzyme-linked immunosorbent assay (Interferon-γ ELISA).

Meanwhile, at least one cytokine including interleukin 2, interleukin 12, interleukin 15 or interleukin 18, which is used as an agent that serves to stimulate the NK cells in the blood sample and artificially activate the NK cells to generate NK cell-secreting cytokines, may be in the form of a fusion protein with a stabilizing peptide.

The interleukin 2, the interleukin 12, the interleukin 15 or the interleukin 18 in the form of a fusion protein with a stabilizing peptide may provide similar biological activity and high storage stability, compared to those of wild-type interleukin 2, interleukin 12, interleukin 15 or interleukin 18. For example, when the cytokine is bound to such a stabilizing peptide, the cytokine has an innate activity while maintaining stability despite changes in environment, such as freeze-drying.

The stabilizing peptide may be bound to the N- or C-terminus of the interleukin 2, interleukin 12, interleukin 15 or interleukin 18, and preparation of such a fusion protein may be performed using known methods of preparing fusion proteins.

According to one exemplary embodiment, a C-terminal acidic tail (acidic tail amino acid sequence of alpha-synuclein, ATS) domain peptide of a synuclein family may be used as the stabilizing peptide that can be bound to the interleukin 2, interleukin 12, interleukin 15 or interleukin 18, but the present invention is not limited thereto. Korean Registered Patent No. 10-0506766 discloses that an ATS peptide endows a fusion partner protein with a resistance against environmental stresses.

According to one exemplary embodiment, the stabilizing peptide that may be used herein includes a stabilizing peptide selected from amino acid residues 103-115, amino acid residues 114-126, amino acid residues 119-140 and amino acid residues 130-140 of the C-terminal acidic tail domain of α-synuclein, amino acid residues 85-134 of the C-terminal acidic tail domain of β-synuclein, amino acid residues 96-127 of the C-terminal acidic tail domain of γ-synuclein, and amino acid residues 96-127 of the C-terminal acidic tail domain of synoretin. In the present invention, an amino acid sequence of an ATS peptide, an ATS peptide and a method of preparing a fusion protein including the same may be performed using a method disclosed in Korean Registered Patent No. 10-0506766. Referring to the following Examples, it is shown that the interleukin 2, interleukin 12, interleukin 15 or interleukin 18 fused with the ATS peptide is highly stable, and expresses a similar activity to a wild-type version when the cytokine is activated by T lymphocyte.

In one embodiment, the step of stimulating NK cells in a blood sample thereby artificially activating the NK cells to generate NK cell-secreting cytokines can be performed in medium containing a carrier protein. The carrier protein plays a role for stabilizing the cytokines such as interleukin 2, interleukin 12, interleukin 15 or interleukin 18 which are used as the agent for stimulating the NK cells in the blood sample and artificially activating the NK cells to generate the NK cell-secreting cytokines, and thereby inducing NK cells to produce more NK cell-secreting cytokines. The carrier protein may, in certain embodiments, be bovine serum albumin or human serum albumin, but is not limited thereto.

Meanwhile, the method of measuring NK cell activity may be used to screen the incidence or relapse of cancer.

The NK cell activity may be measured by comparing an amount of NK cell-secreting cytokines secreted from the artificially activated NK cells with an amount of NK cell-secreting cytokines from the normal person. In this case, when the amount of the NK cell-secreting cytokines is smaller than that of the NK cell-secreting cytokines from the normal person, the NK cell activity is considered to be reduced. Therefore, it is possible to assess the risk of cancer or a relapse of cancer. When NK cell activity is reduced compared to the normal person, a subject may be primarily classified as a patient suspected of suffering from cancer or a patient having a relapse of cancer. Also, the incidence or relapse of cancer may be diagnosed through an additional diagnostic method such as CT, MRI or positron emission tomography (PET) for usually performed diagnosis of cancer, and through a final tissue test. Although the method according to the present invention is not a method of definitively diagnosing cancer, the method has a good merit in that the incidence or relapse of cancer may be primarily screened using blood.

In addition, the present invention provides a kit for measuring NK cell activity, including an agent, such as an agonist or activator that serves to stimulate the NK cells in a blood sample and artificially activate the NK cells to generate NK cell-secreting cytokines. Such a kit for measuring NK cell activity may be used to readily perform the above-mentioned method of measuring NK cell activity.

In the kit for measuring NK cell activity, the agent that serves to stimulate the NK cells and artificially activate the NK cells to generate NK cell-secreting cytokines may be at least one cytokine, LPS or poly I:C, and the cytokine may be selected from the group consisting of interleukin 2, interleukin 12, interleukin 15 and interleukin 18.

In addition to the agent that serves to stimulate the NK cells and artificially activate the NK cells to generate the NK cell-secreting cytokines such as interferon-γ, such a cancer diagnosis kit may include additional components for measurement of NK cell activity, for example an antibody for quantifying the NK cell-secreting cytokines, and a substrate. In one embodiment, the kit of the present invention further comprises at least one antibody selected from the group of an anti-INF-γ antibody, anti-TNF-α antibody and anti-MIP-1β antibody.

The antibody in the kit according to the present invention may be fixed onto a solid substrate. The antibody may be fixed using various methods as described in the literature (*Antibodies*: A Laboratory Manual, Harlow & Lane; Cold Spring Harbor, 1988). The suitable solid substrate may include a cell culture plate, an ELISA plate, a tube and a polymeric film. In addition, the solid substrate includes a bar, a synthetic glass, an agarose bead, a cup, a flat pack, or other films or coatings that are supported by or attached to the solid supports.

Also, the kit according to the present invention may include a reagent used for immunological analysis with an antibody selectively recognizing the NK cell-secreting cytokiness such as interferon-γ. The immunological analysis may include all methods that can measure the binding of an antigen to the antibody according to the present invention. Such methods are known in the art, and include, for example, immunocytochemistry and immunohistochemistry, a radioimmunoassay, ELISA, immunoblotting, a Farr assay, precipitin reaction, a turbidimetric method, immunodiffusion, counter-current electrolysis, single-radical immunodiffusion and immunofluorescence.

The reagent used for the immunological analysis includes a suitable carrier, a label capable of generating a detectable signal, a dissolving agent, and a detergent. Also, when a labeling material is an enzyme, the reagent may include a substrate, which can measure the enzymatic activity, and a reaction stopping agent. The suitable carrier may include, but is not limited to, a soluble carrier, for example one of physiologically available buffers known in the art (for example, PBS) or an insoluble carrier, for example a polymer such as magnetic particles obtained by coating a metal onto polystyrene, polyethylene, polypropylene, polyester, polyacrylonitrile, a fluorine resin, crosslinkable dextran, polysaccharide and latex, and other papers, glasses, metals, agarose, and combinations thereof.

As the label that can generate a detectable signal, an enzyme, a fluorescent material, a luminescent material and a radioactive material may be used. As the enzyme, peroxidase, alkaline phosphatase, β-D-galactosidase, glucose oxidase, malate dehydrogenase, glucose-6-phosphate dehydrogenase, invertase and the like may be used, and isothiocyanate fluorescein or phycobiliprotein may be used as the fluorescent material, isolucinol or lucigenin may be used as the luminescent material, and $I_{131}$, $C_{14}$ or $H_3$ may be used as the radioactive material. In addition to the exemplary materials, however, any materials that can be used for immunological analysis may be used herein.

In addition, the present invention provides a fusion protein including a cytokine bound to a C-terminal acidic tail domain peptide of a synuclein family. Here, the cytokine may be interleukin 2, interleukin 12, interleukin 15 or interleukin 18. As described above, such a fusion protein may be used as the agent that serves to stimulate the NK cells and artificially activate the NK cells to generate NK cell-secreting cytokines, and provides higher stability despite changes in environments such as freeze-drying or long-term storage, compared to a wild-type interleukin 2, interleukin 12, interleukin 15 or interleukin 18.

According to one exemplary embodiment, the fusion protein may be a fusion protein in which the interleukin 2 is bound to the C-terminal acidic tail domain peptide of the synuclein family.

According to another exemplary embodiment, the fusion protein may be a fusion protein in which the interleukin 12 is bound to the C-terminal acidic tail domain peptide of the synuclein family.

According to still another exemplary embodiment, the fusion protein may be a fusion protein in which the interleukin 15 is bound to the C-terminal acidic tail domain peptide of the synuclein family.

According to yet another exemplary embodiment, the fusion protein may be a fusion protein in which the interleukin 18 is bound to the C-terminal acidic tail domain peptide of the synuclein family.

In the fusion protein, the C-terminal acidic tail domain peptide of the synuclein family may also be selected from amino acid residues 103-115, amino acid residues 114-126, amino acid residues 119-140 and amino acid residues 130-140 of the C-terminal acidic tail domain of α-synuclein, amino acid residues 85-134 of the C-terminal acidic tail domain of β-synuclein, amino acid residues 96-127 of the C-terminal acidic tail domain of γ-synuclein, and amino acid residues 96-127 of the C-terminal acidic tail domain of synoretin.

In addition, the present invention provides the use of the fusion protein for activating the NK cells. As described above, such a fusion protein may be used to activate NK cells in blood to promote secretion of NK cell-secreting cytokines.

Therefore, the present invention provides a composition for activating NK cells. Here, the composition includes at least one fusion protein selected from the group consisting of interleukin 2 bound to a C-terminal acidic tail domain peptide of a synuclein family, interleukin 12 bound to the C-terminal acidic tail domain peptide of the synuclein family, interleukin 15 bound to the C-terminal acidic tail domain peptide of the synuclein family, and interleukin 18 bound to the C-terminal acidic tail domain peptide of the synuclein family.

According to one exemplary embodiment, the C-terminal acidic tail domain peptide of the synuclein family may be selected from amino acid residues 103-115, amino acid residues 114-126, amino acid residues 119-140 and amino acid residues 130-140 of the C-terminal acidic tail domain of α-synuclein, amino acid residues 85-134 of the C-terminal acidic tail domain of β-synuclein, amino acid residues 96-127 of the C-terminal acidic tail domain of γ-synuclein, and amino acid residues 96-127 of the C-terminal acidic tail domain of synoretin.

Meanwhile, the composition for activating NK cells may include a buffer capable of keeping and storing the fusion protein, in addition to the cytokines fused with the stabilizing peptide.

Furthermore, the present invention provides a cancer diagnosis kit including at least one fusion protein selected from the group consisting of interleukin 2 bound to a C-terminal acidic tail domain peptide of a synuclein family, interleukin 12 bound to the C-terminal acidic tail domain peptide of the synuclein family, interleukin 15 bound to the C-terminal acidic tail domain peptide of the synuclein family, and interleukin 18 bound to the C-terminal acidic tail domain peptide of the synuclein family. As described above, when a blood sample taken from a subject is incubated with the fusion protein, the NK cells in the blood sample are activated. Therefore, NK cell activity in the subject may be measured by quantifying interferon-γ generated by activation of the NK cells, thereby primarily diagnosing cancer by classifying subjects who have a lower NK cell activity than that of a normal person as patients who are at risk of suffering from cancer or having a relapse of cancer.

According to one exemplary embodiment, the C-terminal acidic tail domain peptide of the synuclein family may be selected from amino acid residues 103-115, amino acid residues 114-126, amino acid residues 119-140 and amino acid residues 130-140 of the C-terminal acidic tail domain of α-synuclein, amino acid residues 85-134 of the C-terminal acidic tail domain of β-synuclein, amino acid residues 96-127 of the C-terminal acidic tail domain of γ-synuclein, and amino acid residues 96-127 of the C-terminal acidic tail domain of synoretin.

In addition to the fusion protein, such a cancer diagnosis kit may include additional components used to perform the diagnostic method according to the present invention, for example an antibody for quantifying the NK cell-secreting cytokines, and a substrate. These components have been described above in connection with the kit for measuring NK cell activity. Instructions for using these components in the above-described method may also be included in the kit.

It will be apparent that these and other features, aspects, and advantages of preferred embodiments of the present invention will be more fully described in the following examples. It is also to be understood that these examples are provided for the purpose of illustration only, and are not intended to limit the scope of the invention. One skilled in the art will understand that other equivalents and modifications can be made without departing from the scope of the invention as claimed.

EXAMPLES

Preparative Example 1

Construction of Expression Vector with Stabilizing Peptide-IL Fusion Protein

In order to prepare IL-2, IL-12 IL-15 or IL-18 fused with a stabilizing peptide, an expression vector was constructed. A peptide containing amino acid residues 119-140 of the α-synuclein (SEQ ID NO: 23; hereinafter, referred to as "SP") was used as the stabilizing peptide. cDNAs of IL2, IL12p35, IL12p40, IL15 and IL-18 were obtained by isolating total RNA from human lymphocytes using a total RNA extraction kit (Invitron Biotechnology) and reverse-transcribing the total RNA using reverse transcriptase (Invitrogen). The resultant cDNA was used as a template, and amplified with PCR using the following primers specific to each cDNA gene:

```
IL2-22-BamH1-F:
                              (SEQ ID NO: 11)
ACAGGATCCCCTACTTCAAGTTCT

IL2-153-Xho-R:
                              (SEQ ID NO: 12)
CACTCTCGAGTCAAGTCAGTGTTGAGAT

IL12-p40-23-BamH:
                              (SEQ ID NO: 13)
GTGGATCCATATGGGAACTGAAGAAAGATG

IL12-p40-328-CT-His:
                              (SEQ ID NO: 14)
ATGGTGATGATGACTGCAGGGCACAGATGCCC

IL12-p35-23-BamH:
                              (SEQ ID NO: 15)
GTGGATCCAGAAACCTCCCCGTGGC

IL12-p35-219-CT-His:
                              (SEQ ID NO: 16)
ATGGTGATGATGGGAAGCATTCAGATAGC

IL15-49-Nde:
                              (SEQ ID NO: 17)
GAGTCAAGCATATGAACTGGGTGAATGTAA

IL15-162-BamH-R:
                              (SEQ ID NO: 18)
GTGGATCCAGAAGTGTTGATGAAC

IL19-37-BamH:
                              (SEQ ID NO: 19)
GTGGATCCTACTTTGGCAAGCTTG

IL18-193-EcoR1:
                              (SEQ ID NO: 20)
AGACTGGAATTCCTAGTCTTCGTTTTG.
```

FIG. 1 is a schematic view showing the constructs of the fusion products of SP with the noted cytokines, including IL2, IL12p35, IL12p40, IL15 and IL-18. As illustrated in the figure, an SP-hIL2 fusion product was constructed by sequentially sub-cloning genes coding for PCR-amplified hIL2 and amino acid residues 119-140 of the α-synuclein into a pRSETA expression vector. An SP-hIL12p40 fusion product was constructed by sequentially sub-cloning genes coding for PCR-amplified hIL12p40 and amino acid residues 119-140 of the α-synuclein into a pVL1393 expression vector. An SP-hIL12p35 fusion product was constructed by sequentially sub-cloning genes coding for PCR-amplified hIL12p35 and amino acid residues 119-140 of the α-synuclein into a pVL1393 expression vector. An hIL15-SP fusion product was constructed by sequentially sub-cloning genes coding for PCR-amplified hIL15 and amino acid residues 119-140 of the α-synuclein into a pRSETA expression vector. An SP-hIL18 fusion product was constructed by sequentially sub-cloning genes coding for PCR-amplified hIL18 and amino acid residues 119-140 of the α-synuclein into a pRSETA expression vector. Sequences of all the constructs were confirmed through DNA sequencing.

Nucleic acid and amino acid sequences of the SP-hIL2 fusion product are set forth in SEQ ID NOS: 1 and 2, respectively. Nucleic acid and amino acid sequences of the SP-hIL12p40 fusion product are set forth in SEQ ID NOS: 3 and 4, respectively. Nucleic acid and amino acid sequences of the SP-hIL12p35 fusion product are set forth in SEQ ID NOS: 5 and 6, respectively. As shown in FIG. 1, a 6×His-tag sequence is contained in each vector for the purpose of isolation and purification of the SP-hIL12p40 fusion product and the SP-hIL12p35 fusion product, which were expressed by viruses. Nucleic acid and amino acid sequences of the hIL15-SP fusion product are set forth in SEQ ID NOS: 7 and 8, respectively. Also, nucleic acid and amino acid sequences of the SP-hIL18 fusion product are set forth in SEQ ID NOS: 9 and 10, respectively.

Preparative Example 2

Expression and Purification of Recombinant SP Fusion Protein

The expression vector constructed to express the recombinant SP-hIL2 protein was transformed into *Escherichia coli* BL21(DE3)RIPL (Invitrogen), and incubated. A culture solution was centrifuged at 10,000 rpm for 10 minutes to obtain a cell pellet. The cell pellet was re-suspended in phosphate buffered saline (PBS, pH 7.4), and then homogenized by sonication. The SP fusion protein expressed in an insoluble form in *E. coli* was subjected to a refolding procedure, and then purified using an ion-exchange resin.

The two expression vectors constructed to express the recombinant SP-hIL12 protein were transfected into insect cell lines, sf21 cells, to produce viral culture solutions, respectively. The two resultant viral culture solutions were transfected into an insect sf21 cell line at the same time to produce a heterodimeric IL12p70 protein in which the IL12p40 was bound to the IL12p35, which was then purified.

The expression vector constructed to express the recombinant hIL15-SP protein was transformed into *E. coli* BL21 (DE3)RIPL (Invitrogen), and then incubated. A culture solution was centrifuged at 10,000 rpm for 10 minutes to obtain a cell pellet. The cell pellet was re-suspended in PBS (pH 7.4), and then homogenized by sonication. The SP fusion protein expressed in a soluble form in *E. coli* was purified using an ion-exchange resin.

The expression vector constructed to express the recombinant SP-hIL18 protein was transformed into *E. coli* BL21 (DE3)RIPL (Invitrogen), and then incubated. A culture solution was centrifuged at 10,000 rpm for 10 minutes to obtain a cell pellet. The cell pellet was re-suspended in PBS (pH 7.4), and then homogenized by sonication. The SP fusion protein expressed in a soluble form in *E. coli* was purified using an ion-exchange resin.

The purified SP fusion protein (3 ug) was electrophoresed using 15% SDS-PAGE to confirm a final purified protein (FIG. 2; (a) SP-hIL2 protein (ATGen, Cat #ATGK04), (b) IL15-SP protein (ATGen, Cat #ATGK06), and (c) SP-IL18 protein (ATGen, Cat #ATGK07)).

Experimental Example 1

Confirming Kinds of Cytokines Capable of Activating NK Cells in Whole Blood 1 ml of whole blood from a normal person and 1 ml of an RPMI1640 medium were put into a 24-well cell culture plate, mixed with 10 ng/ml of each of recombinant human interleukins IL-2, IL-12, IL-15 and IL-18, and then cultured for 24 hours. After the 24-hour culture, a supernatant was taken, and an amount of interferon-γ in the supernatant was measured using a sandwich ELISA method (FIG. 3A). As a result, cytokines secreted by NK cells in the blood sample of the normal person were not detected due to their trace amount, but when the blood sample was treated with at least one of IL-2, IL-12, IL-15 and IL-18, a level of cytokines secreted by the NK cells in the blood sample was increased. When the blood sample was treated with an NK cell stimulator alone, it was seen that a level of interferon-γ in the blood sample was increased especially in the IL-2-treated and IL-12-treated groups (FIG. 3A).

Figure 3:
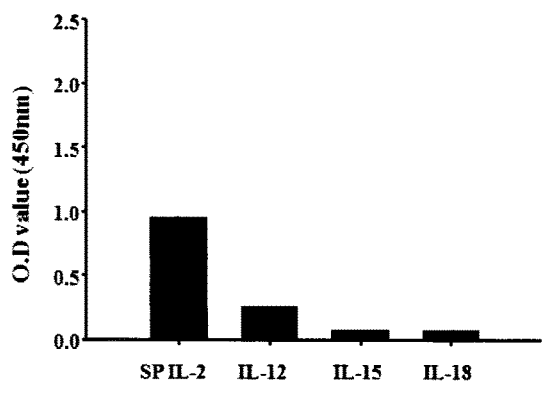
FIGS. 3A-3D show the NK cell activity artificially activated in a normal person through analysis of an amount of generated interferon-γ, when the NK cells are stimulated by single cytokine (FIG. 3A), combined cytokines (FIG. 3B), IL-12 and IL-15 (FIG. 3C), and IL-12 and IL-18 (FIG. 3D).
Figure 3:
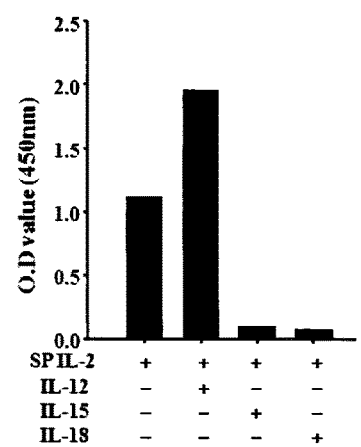
Figure 3:
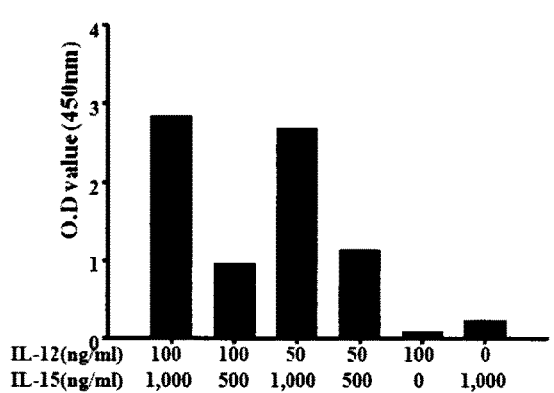
Figure 3:
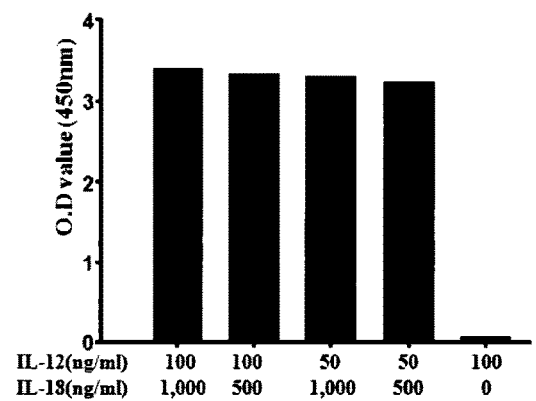

Also, 1 ml of whole blood from a normal person and 1 ml of an RPMI1640 medium were put into a 24-well cell culture plate, treated with various combinations of recombinant human interleukins as shown in FIG. 3B (each 10 ng/ml), and cultured for 24 hours. After the 24-hour culture, a supernatant was taken, and a level of interferon-γ was measured in the same manner as described above. When the whole blood was treated with various combinations of NK cell stimulators, it was seen that a level of interferon-γ was increased especially in the presence of IL-2+IL-12 (FIG. 3B).

Further, in order to measure a level of interferon-γ after the treatment with a combination of IL-12 and IL-15, the whole blood was treated with a concentration of the NK cell stimulator as shown in FIG. 3C, and cultured for 24 hours. After the 24-hour culture, a supernatant was taken, and a level of interferon-γ was measured in the same manner as described above.

In order to measure a level of interferon-γ after the treatment of a combination of IL-12 and IL-18, the whole blood was also treated with a concentration of the NK cell stimulator as shown in FIG. 3D, and then cultured for 24 hours. After the 24-hour culture, a supernatant was taken, and a level of interferon-γ was measured in the same manner as described above.

Experimental Example 2

Confirming Kinds of Cytokines Secreted from NK Cells Artificially Activated with IL-2

Figure 4:
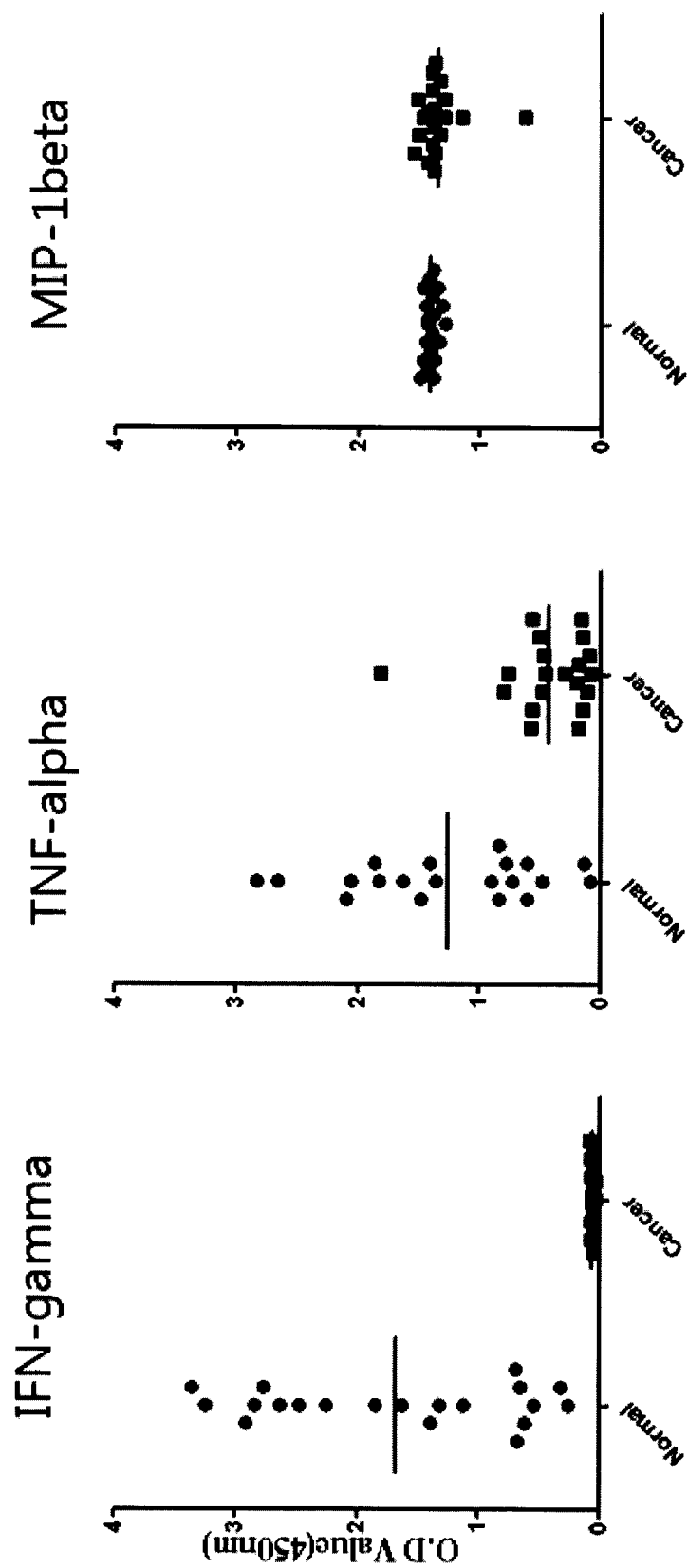
FIG. 4 is a graph showing cytokines secreted from artificially activated NK cells through sandwich ELISA.

Whole blood samples were taken from 61 normal persons and 50 cancer patients. 1 ml of the whole blood and 1 ml of an RPMI1640 medium were put into a 24-well cell culture plate, treated with 10 ng/ml of a recombinant human interleukin SP IL-2, and then cultured for 24 hours. After the 24-hour culture, a supernatant was taken, and levels of interferon-γ, TNF-α and MIP-1β were then measured using a sandwich ELISA method. As a result, it was confirmed that the interferon-γ and TNF-α were secreted from the whole blood of the normal person in a smaller amount than that of the cancer patient, but the MIP-1β was secreted from the whole blood samples of the normal person and the cancer patient, as shown in FIG. 4.

In the case of in vitro diagnostic reagents used in a disease test, a variety of validation techniques were used. In general, a normal range and a cut-off assay were used herein. The normal range is a reference range which is used to measure an average value and a standard deviation of each group of samples, and the cut-off assay is a method of measuring clinical sensitivity and specificity by calculating an estimated value of an in vitro diagnostic reagent. The clinical sensitivity means a probability of being proven to show positive results of a diagnostic test when a patient suffers from a disease, and the clinical specificity means a probability of being proven to show negative results of the diagnostic test when a patient does not suffer from a disease.

Assume that, when a cut-off value is more than 10% and less than 10%, the cut-off value is set to positive and negative values, respectively. Then, the clinical sensitivity and clinical specificity were measured using a cut-off assay. The results are listed in Table 1.

TABLE 1

|  | IFN-γ | TNF-α | MIP-1β |
| --- | --- | --- | --- |
| Clinical sensitivity (%) | 98.4 | 90.9 | 100 |
| Clinical specificity (%) | 98.0 | 69.0 | 50 |

In the groups of cancer patients and normal persons, IFN-γ was measured to have a sensitivity of 98.4% and a specificity of 98%. Although TNF-α was measured to have a sensitivity of 90.9% and a specificity of 69%, which were lower than those of IFN-γ, cancer diagnostic kits developed up to date have a specificity of at most 20 to 30%. Thus, it is expected that the TNF-α having a specificity of approximately 70% or more may also be used as a marker for cancer diagnostic kits to measure the NK cell activity.

Experimental Example 3

Comparison of Stabilities of SP IL-2 and IL-2

Figure 5:
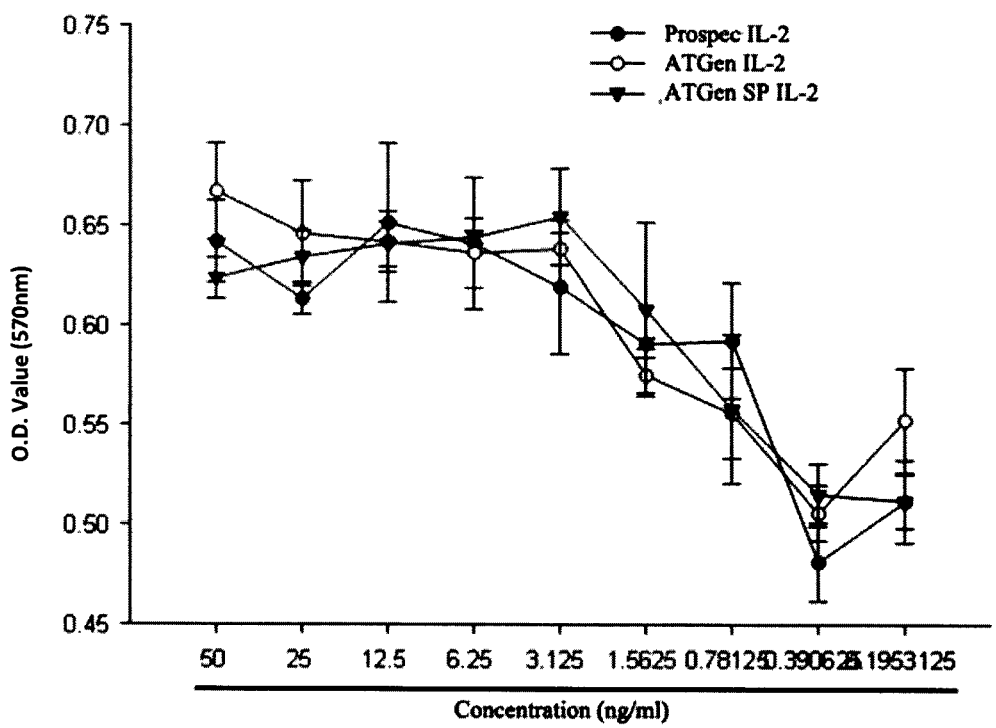
FIGS. 5A-5B show a comparison of the protein activity (FIG. 5A) and stability (FIG. 5B) between SP IL-2 and IL-2.
Figure 5:
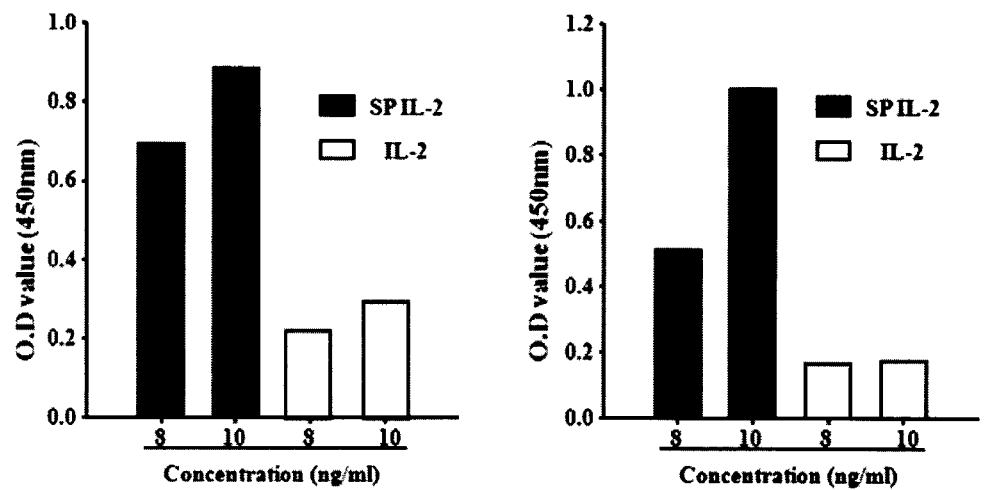

In order to compare the stabilities of SP IL-2 and IL-2, whole blood samples were taken from two persons. 1 ml of each obtained whole blood sample and 1 ml of an RPMI1640 medium were put into a 24-well cell culture plate, and SP IL-2 and IL-2 were then added, thoroughly mixed, and then cultured for 24 hours. After the 24-hour culture, a supernatant was taken, and a level of interferon-γ was measured using a sandwich ELISA method. From the results of the IL-2 and SP IL-2 activity assays, it was seen that there was no difference in activities of the two proteins (FIG. 5A). However, when the whole blood was treated with SP IL-2 rather than IL-2 under the whole blood culture conditions, respectively, it could be confirmed that the NK cells were activated by SP IL-2, thereby increasing a level of the interferon-γ (FIG. 5B). This indicates that there is no difference in activities of the two proteins but the stability of IL-2 is increased due to application of SP.

Experimental Example 4

Comparison of NK Cell Activity from Normal Persons and Cancer Patients According to Conditions for Simulation of NK Cells 1 ml of each of whole blood samples taken from 20 normal persons and 48 terminal (stage 3 to 4) cancer patients, and 1 ml of an RPMI1640 medium were put into a 24-well culture plate, each sample was divided into two sub-groups, and the sub-groups were treated with SP IL-2 (10 ng/ml) (Condition A) and SP IL-2 (5 ng/ml)+IL-12 (5 ng/ml) (Condition B), respectively, and then cultured for 24 hours. After the culture, a supernatant was taken, and a level of interferon-γ was measured using a sandwich ELISA method.

Figure 6:
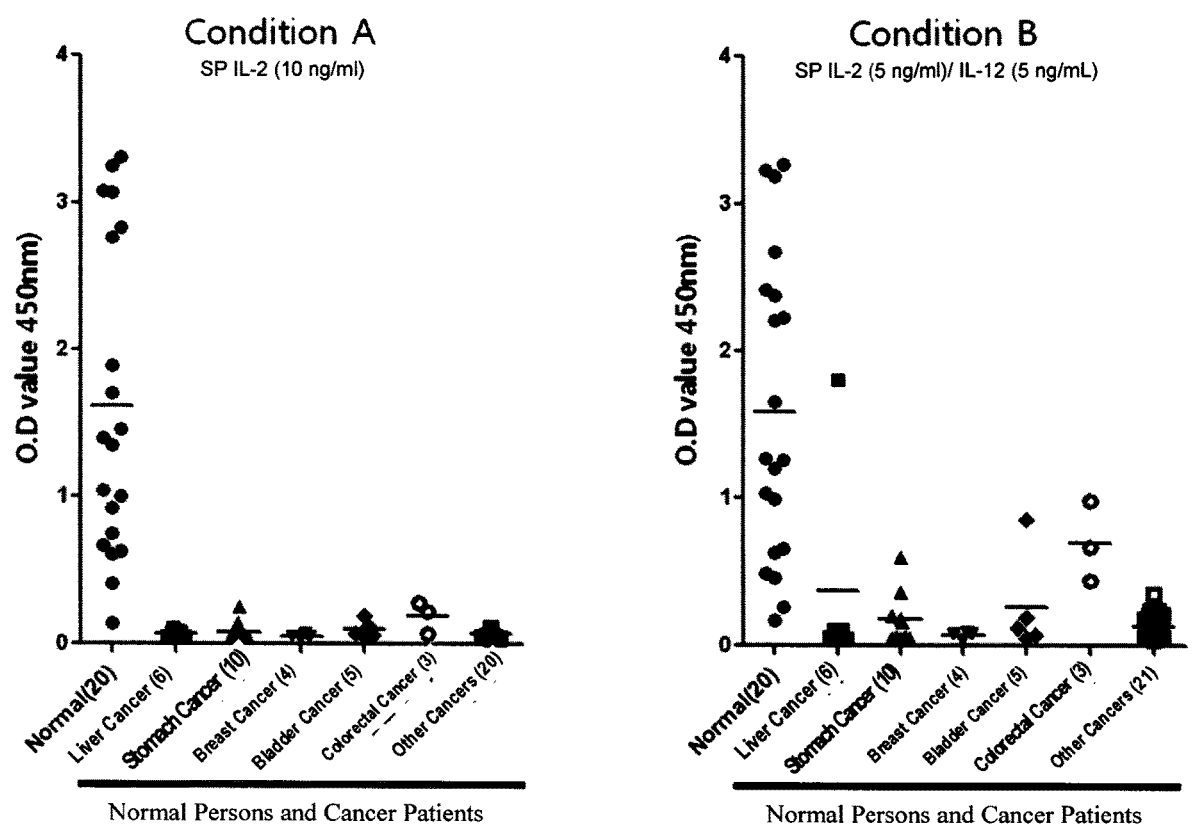
FIG. 6 shows the activity of NK cells in normal persons and cancer patients which are treated with SP IL-2 (10 ng/ml) (FIG. 6—Condition A), and SP IL-2 (5 ng/ml)+IL-12 (5 ng/ml) (FIG. 6—Condition B), separately.

As a result, it was seen that approximately 90% of the normal persons had a high interferon-γ level but most of the cancer patients had a low interferon-γ level in the case of Condition A, as shown in FIG. 6. In the case of Condition B, it was also seen that the normal persons had a high interferon-γ level but most of the cancer patients had a low interferon-γ level. However, the high interferon-γ level was higher in the cancer patients in the case of Condition B, compared to the case of Condition A. When the whole blood sample is treated with SP IL-2 alone, only the NK cells are specifically activated (see the following Experimental Example 5 and FIG. 7), but the NK cells are likely to be activated together with T cells when the whole blood sample is treated with a combination of SP IL-2 and IL-12, and thus a level of interferon-γ is likely to be increased by activation of the T cells. Therefore, a high interferon-γ level is considered to be possible to observe in some of the cancer patients in which the T cell activity remains. When the cancer patients had a low interferon-γ level even when treated with Condition B, it could be deduced that the anticancer immunity of the NK cells and the general systemic immunities were decreased in the cancer patients. This is considered to be used as an important marker for determining the cancer progression or prognosis.

Experimental Example 5

Figure 7:
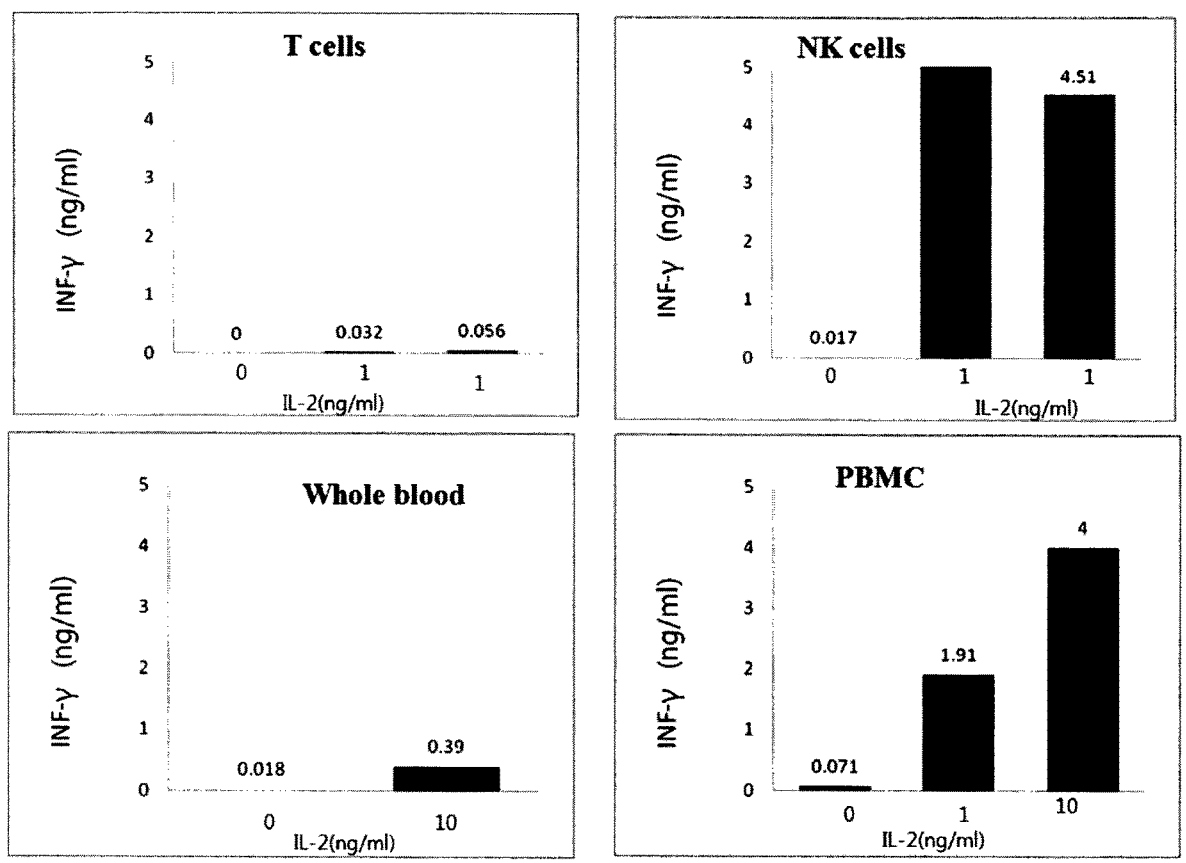
FIG. 7 is a graph showing the capability of NK cells to secrete interferon-γ in T cells, NK cells, whole blood and PBMC according to the stimulus of IL2.

Comparison of NK Cell Activity from Normal Persons and Cancer Patient by IL2 According to Type of Blood Samples In order to determine the difference in interferon-γ secretion capability by IL2 according to the type of blood samples from normal persons, the following experiment was performed. (a) The interferon-γ secretion capability of the NK cells on 1 ng/ml of IL2 from the T cells, (b) the interferon-γ secretion capability of the NK cells on 1 ng/ml of IL2 from the NK cells, (c) the interferon-γ secretion capability of the NK cells on 1 ng/ml of IL2 from the whole blood, and (d) the interferon-γ secretion capability of the NK cells according to concentration of IL2 from the PBMC were measured. The results are shown in FIG. 7. The interferon-γ was measured in the same manner as described above. As a result, since the amount of the interferon-γ secreted by activation of the IL2 in the T cells was changed, but not highly different from that of the interferon-γ of an untreated group, the T cells were not suitable for use as a blood sample. In the whole blood, the PBMCs and the NK cells, there is a significant difference in amount of interferon-γ, compared to that of the interferon-γ of the untreated group. Therefore, the whole blood, the PBMCs and the NK cells were evaluated to be suitable blood samples to apply to the method and kit according to the present invention.

Experimental Example 6

Comparison of NK Cell Activity from Normal Persons by LPS

Figure 8:
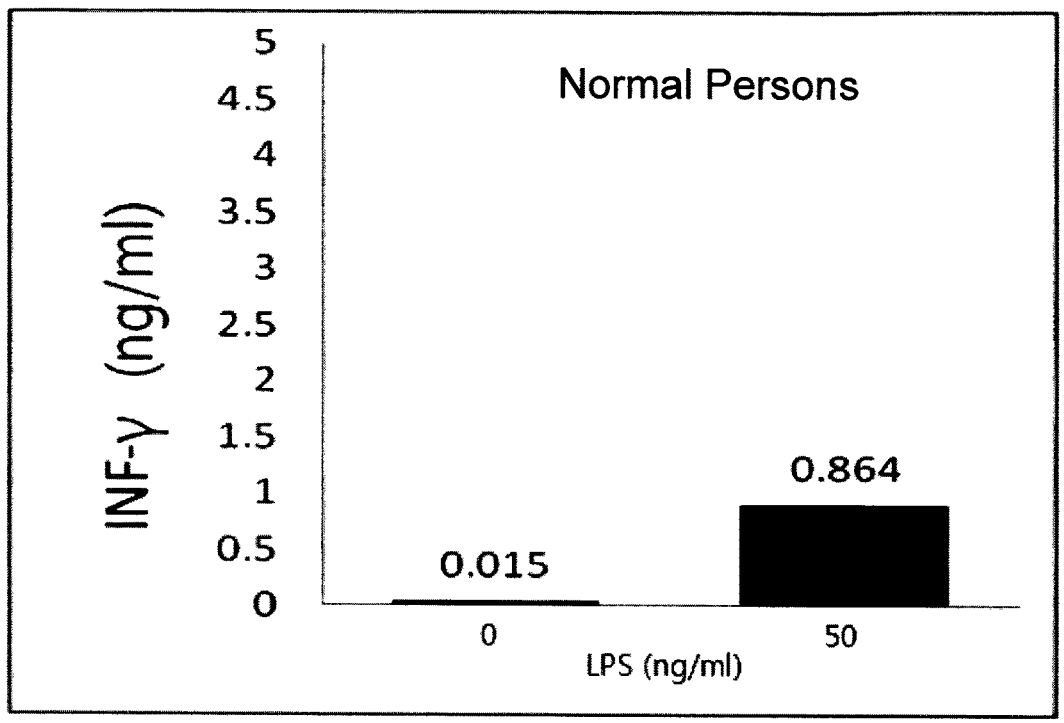
FIG. 8 is a graph showing a variation in amount of interferon-γ secreted from NK cells of a normal person, as stimulated by LPS.

As another example of the agent that serves to stimulate NK cells in a blood sample and artificially activate the NK cells to generate interferon-γ, LPS was used to measure an amount of interferon-γ from human whole blood. As shown in FIG. 8, it was revealed that secretion of interferon-γ was induced by 50 ng/ml of LPS, which indicates that the NK cells may be artificially activated to generate the interferon-γ even when the NK cells are stimulated with a non-specific agonist such as LPS.

Experimental Example 7

Stimulation of NK Cells by hIL12 and hIL15 Fused with Stabilizing Peptide

As a tube for incubating NK cells, a tube (BD) containing an anticoagulant, sodium heparin, was purchased and used to prevent coagulation of blood. 5 ml of whole blood was taken and put into the tube containing the anticoagulant (sodium heparin). 1 ml of the obtained whole blood was mixed with RPIM1640 medium, and activators of NK cells, SP-hIL2/hIL12 were added thereto. The resultant mixture was incubated at 37° C. for 16 to 24 hours. The stimulation of the NK cells in the whole blood by the SP hIL2 fused with the stabilizing peptide and hIL12 was determined by measuring an amount of the interferon-γ in blood incubated according to the method described in the above Experimental Example.

Figure 9:
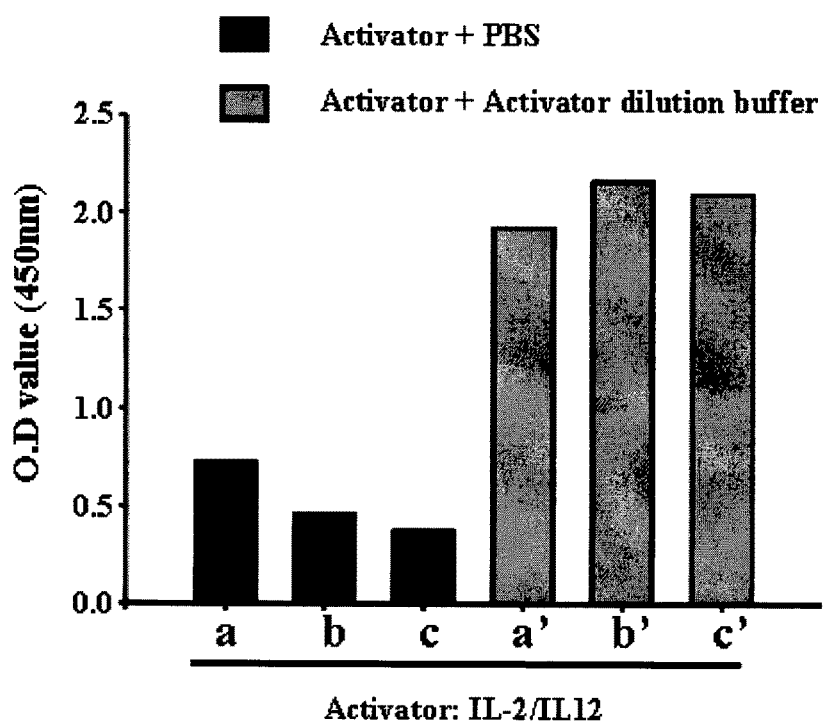
FIG. 9 is a graph showing a variation in capability of NK cells to secrete interferon-γ according to concentrations of IL12 and IL15 treated and difference in compositions of media.

Meanwhile, the amount of the interferon-γ secreted according to the culture conditions of the whole blood was measured. As shown in FIG. 9, it was revealed that the interferon-γ secretion capability of the NK cells was increased when the NK cells were incubated in PBS supplemented with a carrier protein such as bovine serum albumin, compared to when the NK cells were incubated in PBS.

Experimental Example 8

Difference of Interferon-γ Secretion According to the Progress Stage of Cancer

In order to determine an amount of the interferon-γ secreted according to the progress stage of cancer, whole blood from cancer patient 1 (a patient completely recovered from breast cancer), cancer patient 2 (a patient suspected of suffering from brain cancer), and a normal person was incubated for 24 hours in RPMI1640 medium supplemented with 100 ng/ml of IL12 and 1000 ng/ml of IL15, and amounts of the secreted interferon-γ were measured as described above. Also, the whole blood was subjected to flow cytometry.

Figure 10:
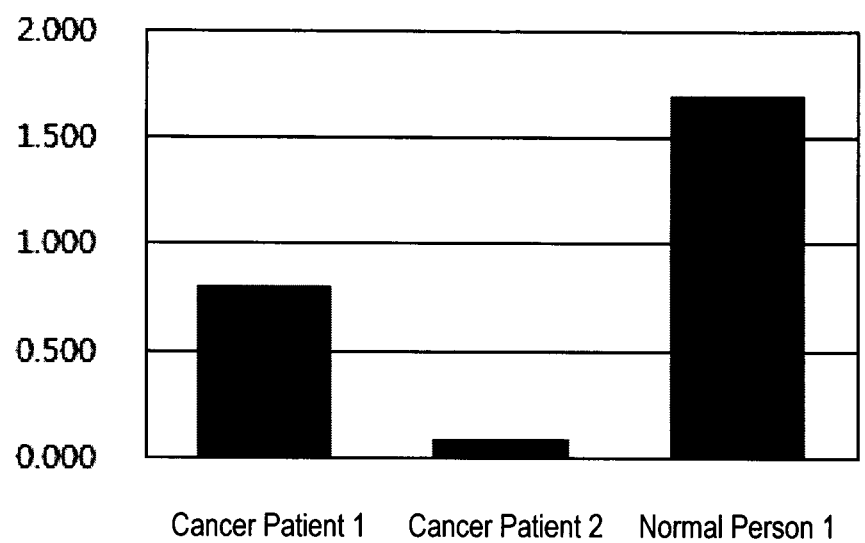
FIG. 10 is a graph showing a variation in amount of secreted interferon-γ according to the progress stage of cancer.

As a result, the interferon-γ secretion capabilities were confirmed in order of the normal person, the cancer patient 1 and the cancer patient 2, as shown in FIG. 10. Therefore, it was confirmed that the amounts of interferon-γ secreted according to the progress stage of cancer were different.

was performed three times. The 96-well microliter ELISA plate coated with the primary antibody was sealed, and stored at 4° C. for use.

An interferon-γ standard solution (PBS containing 200 ng of recombinant human interferon-γ (ATGen, Cat #IFG4001) and 0.05% Proclin 300) was diluted and divided at a dose of 100 ul/well into the 96-well microtiter ELISA plate coated with the primary antibody, and the patient's serum prepared in the experimental stage was divided at a dose of 100 ul/well, and then kept at room temperature for 2 hours.

TABLE 2

|   | 1     | 2     | 3  | 4  | 5  | 6  | 7  | 8  | 9  | 10 | 11 | 12 |
|---|-------|-------|----|----|----|----|----|----|----|----|----|----|
| A | Blank | Blank | UK | UK | UK | UK | UK | UK | UK | UK | UK | UK |
| B | Blank | Blank | UK | UK | UK | UK | UK | UK | UK | UK | UK | UK |
| C | S1    | S1    | UK | UK | UK | UK | UK | UK | UK | UK | UK | UK |
| D | S2    | S2    | UK | UK | UK | UK | UK | UK | UK | UK | UK | UK |
| E | S3    | S3    | UK | UK | UK | UK | UK | UK | UK | UK | UK | UK |
| F | S4    | S4    | UK | UK | UK | UK | UK | UK | UK | UK | UK | UK |
| G | S5    | S5    | UK | UK | UK | UK | UK | UK | UK | UK | UK | UK |
| H | S6    | S6    | UK | UK | UK | UK | UK | UK | UK | UK | UK | UK |

Blank: buffer only,
S1-S6: serially diluted standard, and
UK (unknown): patient serum From these facts, it was seen that the method according to the present invention may be used to measure an amount of the interferon-γ secreted by the NK cells in the blood sample, thereby predicting the incidence and progress stage of cancer, or predicting the relapse of cancer.

Experimental Example 9

Quantification of Interferon-γ Generated by Stimulation of NK Cells

As a tube for incubating NK cells, a tube (BD) containing an anticoagulant, sodium heparin, was purchased and used to prevent coagulation of blood. 5 ml of whole blood was taken from eight normal persons and put into the tube containing the anticoagulant (sodium heparin). 1 ml of the obtained whole blood was mixed with RPIM1640 medium, and SP-hIL12/hIL15-SP bound to stabilizing peptide were added thereto. The resultant mixture was incubated at 37° C. for 16 to 24 hours.

Whole blood from eight normal persons incubated at 37° C. was centrifuged at 1500 to 2000 g to obtain serum as a supernatant. Then, 150 to 200 ul of the serum was taken and subjected to interferon-γ ELISA. 0.05% Tween primary antibody (anti-human interferon-γ monoclonal antibody, ATGen Cat #ATGK02) was diluted with a coating buffer (0.1 sodium carbonate, pH 9.5) at a ratio of 1:1000. The diluted primary antibody was divided onto a 96-well microtiter ELISA plate (Nune MAXISORP™; NUNC, Naperville, Ill.) at a dose of 100 and kept at 4° C. for 16 to 18 hours. Thereafter, a solution in the plate was removed, and the plate was washed with a washing solution (PBS containing 0.05% Tween 20) at a dose of 400 ul/well. In this case, the washing was performed three times. Then, PBS containing 10% fetal bovine serum (FBS) was divided at a dose of 300 ul/well, and kept at room temperature for 1 hour. Thereafter, a solution in the plate was removed, and the plate was washed with PBST (a PBS solution containing 0.05% Tween 20) at a dose of 400 ul/well. In this case, the washing After 2 hours, a solution in the 96-well microtiter ELISA plate was removed, and the plate was washed with a washing solution at a dose of 400 ul/well. In this case, the washing was performed three times. Then, a secondary antibody (biotinylated anti-human interferon-γ monoclonal antibody (ATGen Cat #ATGK03)) was diluted with a dilute solution at a ratio of 1:500, divided at a dose of 100 ul/well, and then kept at room temperature for 1 hour. Thereafter, solution in the plate was removed, and the plate was washed three times with a washing solution at a dose of 400 ul/well. An HRP-conjugated streptavidin solution (Thermo Scientific, Cat #21130) was diluted with a dilute solution at a ratio of 1:3000, divided at a dose of 100 ul/well, and then kept at room temperature for 30 minutes. Then, the diluted HRP-conjugated streptavidin solution was divided into the ELISA plate, and incubated for 1 hour. After the one-hour incubation, a solution in the 96-well microtiter ELISA plate was removed, and the plate was washed three times with a washing solution at a dose of 400 ul/well.

1 mg of tetramethylbenzidine (TMB) was dissolved in 1 ml of dimethylsulfoxide (DMSO), and the resultant mixture was diluted with 9 ml of 0.05 M phosphate citrate buffer to prepare a substrate solution. Then, the substrate solution was divided into the plate at a dose of 100 ul/well, and kept at room temperature for 30 minutes.

A reaction-stopping solution (a 2 N dilute sulfuric acid solution) was divided at a dose of 100 ul/well to stop the reaction, and the resultant reaction solution was measured at 450 nm using an ELISA reader.

Figure 11:
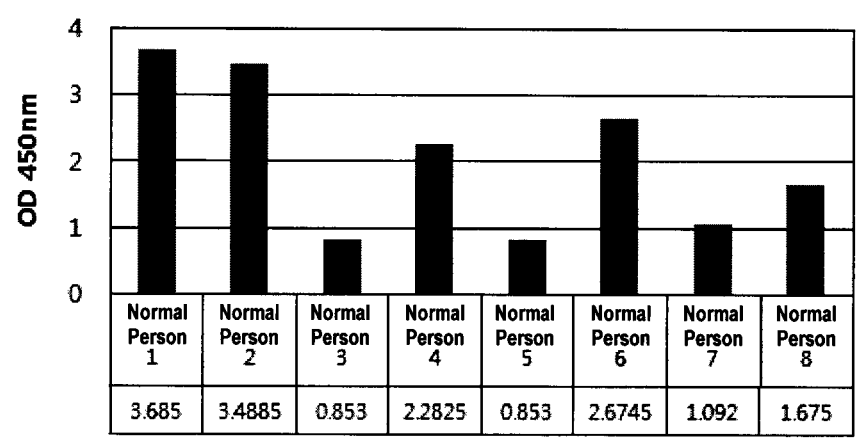
FIG. 11 shows the results of analysis of interferon-γ generated from NK cells of a normal person stimulated by cytokines using an ELISA plate.

The interferon-γ secretion capabilities of the NK cells measured using the whole blood from eight normal persons are shown in FIG. 11. These results indicate that, when the whole blood is stimulated by the cytokine, immune cells present in blood are effectively activated to induce secretion of interferon-γ.

Figure 12:
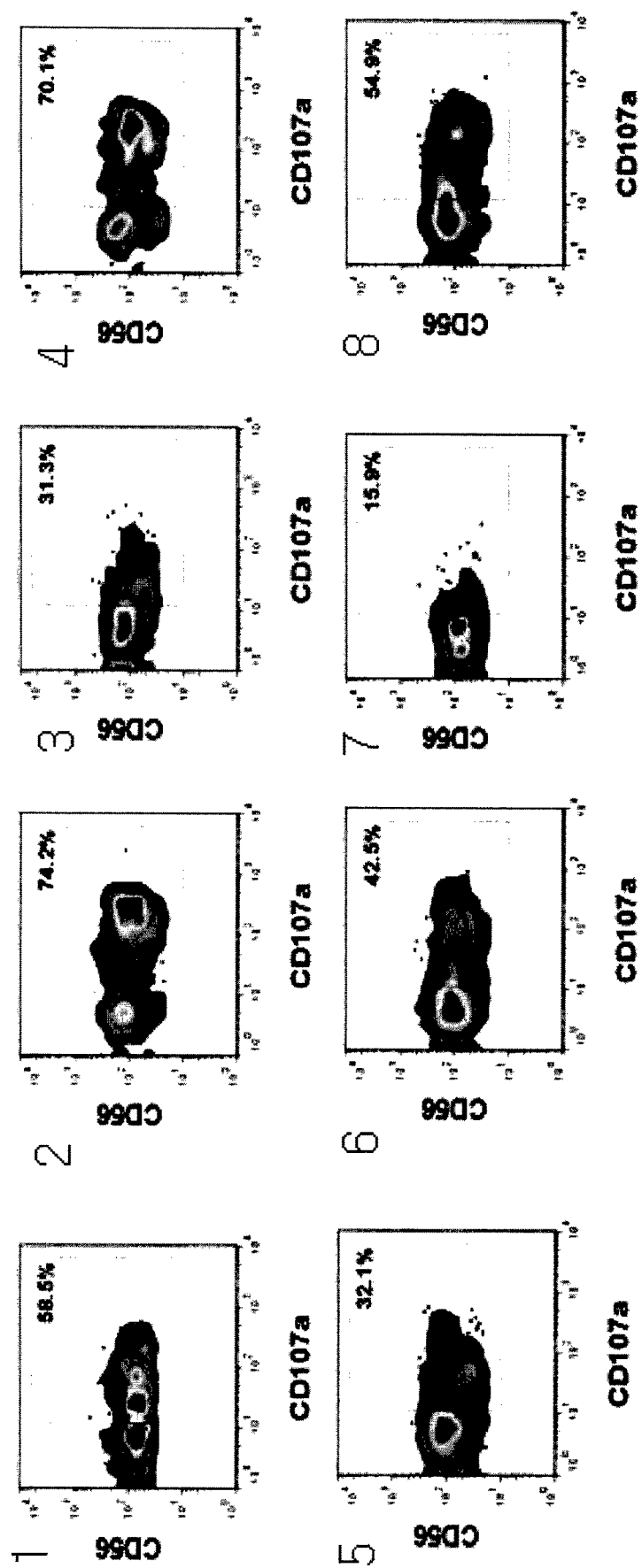
FIG. 12 shows the flow cytometric results of whole blood from normal persons stimulated by cytokines.

Furthermore, after the whole blood from the eight normal persons was stimulated by the cytokine, the whole blood was subjected to flow cytometry. The results are shown in FIG. 12. From these results, it was revealed that the NK cells expressed cytotoxicity as the NK cells were activated by the stimulation of the whole blood. CD56 is a marker of the NK cells, and CD107a is a marker indicating that the NK cells secrete cytotoxic granules. Since the results of secretion of the interferon-γ of FIG. 11 significantly correlate with the cytotoxicity results by the NK cells of FIG. 12, it was seen that the interferon-γ secretion capability of the NK cells by the stimulation of the whole blood indirectly expresses the cytotoxicity of the NK cells.

According to the present invention, the incidence or relapse of cancer may be diagnosed by monitoring changes in an in vivo immune system and measuring NK cell activity in blood, for instance in a subject with or suspected of having cancer. The present invention may therefore be useful in predicting the incidence or relapse of cancer using a blood sample from a subject.

While exemplary embodiments have been disclosed herein, it should be understood that other variations may be possible. Such variations are not to be regarded as a departure from the scope of exemplary embodiments of the present application, and all such modifications as would be obvious to one skilled in the art are intended to be included within the scope of the following claims.

All documents cited herein are hereby incorporated by reference.

What is claimed is:

1. A method of measuring natural killer (NK) cell activity, comprising:
   stimulating NK cells in a whole blood sample by incubating the whole blood sample with a composition comprising interleukin 15 and interleukin 12, thereby artificially activating the NK cells to generate and secrete NK cell-secreting cytokines; and
   measuring an amount of the NK cell-secreting cytokines secreted into the whole blood sample and using the amount as a measure of NK cell activity;
   wherein the whole blood sample is a human whole blood sample.

2. The method according to claim 1, wherein the composition further comprises interleukin 2.

3. The method according to claim 1, wherein the NK cell-secreting cytokines are selected from the group consisting of interferon-gamma (IFN-γ), tumor necrosis factor-alpha (TNF-α) and macrophage inflammatory protein-1β (MIP-1β).

4. The method according to claim 1, wherein the NK cell-secreting cytokine is interferon-gamma (IFN-γ).

5. The method according to claim 1, wherein the NK cell-secreting cytokine is tumor necrosis factor-alpha (TNF-α).

6. The method according to claim 1, wherein the measuring of the amount of the NK cell-secreting cytokines is performed by enzyme-linked immunosorbent assay (ELISA) or other immunoassay.

7. The method according to claim 1, wherein the IL-15 and IL-12 are in the form of a fusion protein with a stabilizing peptide.

8. The method according to claim 7, wherein the stabilizing peptide is a C-terminal acidic tail domain peptide of a synuclein family.

9. The method according to claim 8, wherein the stabilizing peptide comprises amino acid residues 103-115 (SEQ ID NO: 22), amino acid residues 114-126 (SEQ ID NO: 23), amino acid residues 119-140 (SEQ ID NO: 24) or amino acid residues 130-140 (SEQ ID NO: 25) of the C-terminal acidic tail domain of α-synuclein, amino acid residues 85-134 of the C-terminal acidic tail domain of β-synuclein (SEQ ID NO: 27), amino acid residues 1-127 of γ-synuclein (SEQ ID NO: 28), or amino acid residues 96-127 of the C-terminal acidic tail domain of γ-synuclein (SEQ ID NO: 29).

10. The method according to claim 1, wherein the step of stimulating NK cells in a whole blood sample thereby artificially activating the NK cells to generate and secrete NK cell-secreting cytokines is performed in solution containing a carrier protein.

11. The method according to claim 1, wherein the IL-12 is in the form of a fusion protein with a stabilizing peptide, wherein the fusion protein comprises an amino acid sequence of SEQ ID NO: 4 or 6, or the IL-15 is in the form of a fusion protein with a stabilizing peptide, wherein the fusion protein comprises an amino acid sequence of SEQ ID NO: 8.

12. The method according to claim 2, wherein interleukin 2 is in the form of a fusion protein with a stabilizing peptide.

13. The method according to claim 1, wherein the interleukin 15 is in the form of a fusion protein with a stabilizing peptide.

14. A method of measuring natural killer (NK) cell activity, comprising:
stimulating NK cells in a whole blood sample by incubating the whole blood sample with an agent comprising the isolated stimulating cytokine interleukin 2 in the form of a fusion protein with a stabilizing peptide, thereby artificially activating the NK cells to generate and secrete NK cell-secreting cytokines; and
measuring an amount of the NK cell-secreting cytokines secreted into the whole blood sample and using the amount as a measure to evaluate NK cell activity;
wherein the whole blood sample is a human whole blood sample.

15. The method of claim 14, wherein the NK cell-secreting cytokine is interferon-gamma (IFN-γ), tumor necrosis factor-alpha (TNF-α), or both.

16. A method of measuring natural killer (NK) cell activity, comprising:
stimulating NK cells in a whole blood sample by incubating the whole blood sample with an agent comprising at least one isolated stimulating cytokine selected from the group consisting of interleukin 2 and interleukin 15, thereby artificially activating the NK cells to generate and secrete NK cell-secreting cytokines; and
measuring an amount of the NK cell-secreting cytokines secreted into the whole blood sample and using the amount as a measure to evaluate NK cell activity;
wherein the at least one stimulating cytokine is in the form of a fusion protein with a stabilizing peptide.

17. The method according to claim 16, wherein the stimulation of the NK cells is performed by incubating the whole blood sample with at least interleukin 2 in the form of a fusion protein with a stabilizing peptide.

18. The method according to claim 16, wherein the stimulation of the NK cells is performed by incubating the whole blood sample with at least interleukin 15 in the form of a fusion protein with a stabilizing peptide.

19. The method according to claim 16, wherein the stimulation of the NK cells is performed by incubating the whole blood sample with interleukin 2 and interleukin 12.

20. The method according to claim 16, wherein the stimulation of the NK cells is performed by incubating the whole blood sample with interleukin 15 and interleukin 12.

21. The method according to claim 16, wherein the NK cell-secreting cytokines are selected from the group consisting of interferon-gamma (IFN-γ), tumor necrosis factor-alpha (TNF-α) and macrophage inflammatory protein-1β (MIP-1β).

22. The method according to claim 16, wherein the NK cell-secreting cytokine is interferon-gamma (IFN-γ).

23. The method according to claim 16, wherein the NK cell-secreting cytokine is tumor necrosis factor-alpha (TNF-α).

24. The method according to claim 16, wherein the stabilizing peptide is a C-terminal acidic tail domain peptide of a synuclein family.

25. The method according to claim 16, wherein the stabilizing peptide comprises amino acid residues 103-115 (SEQ ID NO: 22), amino acid residues 114-126 (SEQ ID NO: 23), amino acid residues 119-140 (SEQ ID NO: 24) or amino acid residues 130-140 (SEQ ID NO: 25) of the C-terminal acidic tail domain of α-synuclein, amino acid residues 85-134 of the C-terminal acidic tail domain of β-synuclein (SEQ ID NO: 27), amino acid residues 1-127 of γ-synuclein (SEQ ID NO: 28), or amino acid residues 96-127 of the C-terminal acidic tail domain of γ-synuclein (SEQ ID NO: 29).

26. The method according to claim 16, wherein the fusion protein comprises an amino acid sequence of SEQ ID NO: 2 or SEQ ID NO: 8.

27. The method according to claim 16, wherein the stimulation of the NK cells is performed by incubating the whole blood sample with interleukin 2 in the form of a fusion protein with a stabilizing peptide.

28. The method according to claim 16, wherein the stimulation of the NK cells is performed by incubating the whole blood sample with interleukin 15 in the form of a fusion protein with a stabilizing peptide.

29. The method according to claim 27, wherein the NK cell-secreting cytokine is interferon-gamma (IFN-γ).

30. The method according to claim 28, wherein the NK cell-secreting cytokine is interferon-gamma (IFN-γ).

31. The method of claim 1, wherein the stimulation of the NK cells is performed by incubating the whole blood sample with interleukin 2 in the form of a fusion protein with a stabilizing peptide, and wherein the NK cell-secreting cytokine is interferon-gamma (IFN-γ).

32. The method of claim 31, wherein the stabilizing peptide comprises the amino acid sequence of SEQ ID NO: 24.

33. The method of claim 32, wherein the interleukin 2 in the form of a fusion protein with a stabilizing peptide comprises the amino acid sequence of SEQ ID NO: 2.

* * * * *

UNITED STATES PATENT AND TRADEMARK OFFICE
CERTIFICATE OF CORRECTION

| | | |
|---|---|---|
| PATENT NO. | : 11,442,069 B2 | Page 1 of 1 |
| APPLICATION NO. | : 13/985301 | |
| DATED | : September 13, 2022 | |
| INVENTOR(S) | : Jae Myun Lee et al. | |

It is certified that error appears in the above-identified patent and that said Letters Patent is hereby corrected as shown below:

On the Title Page

At the Name of item (73), the Assignee:
"ATGEN CO. LTD. GYEONGGI-DO, KR"
Should be replaced with:
—NKMAX Co., Ltd. GYEONGGI-DO, KR—.

Signed and Sealed this
Tenth Day of October, 2023

Katherine Kelly Vidal
*Director of the United States Patent and Trademark Office*

SEQUENCE LISTING

```
<160> NUMBER OF SEQ ID NOS: 29

<210> SEQ ID NO 1
<211> LENGTH: 474
<212> TYPE: DNA
<213> ORGANISM: Artificial Sequence
<220> FEATURE:
<223> OTHER INFORMATION: SP-hIL2 fusion coding sequence

<400> SEQUENCE: 1
atggaccctg acaatgaggc ttatgaaatg ccttctgagg aagggtatca agactacgaa      60
cctgaagccg gatcccctac ttcaagttct acaaagaaaa cacagctaca actggagcat     120
ttactgctgg atttacagat gattttgaat ggaattaata attacaagaa tcccaaactc     180
accaggatgc tcacatttaa gttttacatg cccaagaagg ccacagaact gaaacatctt     240
cagtgtctag aagaagaact caaacctctg gaggaagtgc taaatttagc tcaaagcaaa     300
aactttcact taagacccag ggacttaatc agcaatatca acgtaatagt tctggaacta     360
aagggatctg aaacaacatt catgtgtgaa tatgctgatg agacagcaac cattgtagaa     420
tttctgaaca gatggattac cttttgtcaa agcatcatct caacactgac ttga            474

<210> SEQ ID NO 2
<211> LENGTH: 157
<212> TYPE: PRT
<213> ORGANISM: Artificial Sequence
<220> FEATURE:
<223> OTHER INFORMATION: SP-hIL2 fusion polypeptide

<400> SEQUENCE: 2

Met Asp Pro Asp Asn Glu Ala Tyr Glu Met Pro Ser Glu Glu Gly Tyr
1               5                   10                  15

Gln Asp Tyr Glu Pro Glu Ala Gly Ser Pro Thr Ser Ser Ser Thr Lys
            20                  25                  30

Lys Thr Gln Leu Gln Leu Glu His Leu Leu Leu Asp Leu Gln Met Ile
        35                  40                  45

Leu Asn Gly Ile Asn Asn Tyr Lys Asn Pro Lys Leu Thr Arg Met Leu
    50                  55                  60

Thr Phe Lys Phe Tyr Met Pro Lys Lys Ala Thr Glu Leu Lys His Leu
65                  70                  75                  80

Gln Cys Leu Glu Glu Glu Leu Lys Pro Leu Glu Glu Val Leu Asn Leu
                85                  90                  95

Ala Gln Ser Lys Asn Phe His Leu Arg Pro Arg Asp Leu Ile Ser Asn
            100                 105                 110

Ile Asn Val Ile Val Leu Glu Leu Lys Gly Ser Glu Thr Thr Phe Met
        115                 120                 125

Cys Glu Tyr Ala Asp Glu Thr Ala Thr Ile Val Glu Phe Leu Asn Arg
    130                 135                 140
```

Trp Ile Thr Phe Cys Gln Ser Ile Ile Ser Thr Leu Thr
145                 150                 155

<210> SEQ ID NO 3
<211> LENGTH: 1014
<212> TYPE: DNA
<213> ORGANISM: Artificial Sequence
<220> FEATURE:
<223> OTHER INFORMATION: SP-hIL12p40 fusion coding sequence

<400> SEQUENCE: 3

| | | | | | |
|---|---|---|---|---|---|
| atggaccctg | acaatgaggc | ttatgaaatg | ccttctgagg | aagggtatca | agactacgaa | 60 |
| cctgaagccg | gatccatatg | ggaactgaag | aaagatgttt | atgtcgtaga | attggattgg | 120 |
| tatccggatg | cccctggaga | aatggtggtc | ctcacctgtg | acacccctga | agaagatggt | 180 |
| atcacctgga | ccttggacca | gagcagtgag | gtcttaggct | ctggcaaaac | cctgaccatc | 240 |
| caagtcaaag | agtttggaga | tgctggccag | tacacctgtc | acaaaggagg | cgaggttcta | 300 |
| agccattcgc | tcctgctgct | tcacaaaaag | gaagatggaa | tttggtccac | tgatattta | 360 |
| aaggaccaga | agaacccaa | aataagacc | tttctaagat | gcgaggccaa | gaattattct | 420 |
| ggacgtttca | cctgctggtg | gctgacgaca | atcagtactg | atttgacatt | cagtgtcaaa | 480 |
| agcagcagag | gctcttctga | cccccaaggg | gtgacgtgcg | gagctgctac | actctctgca | 540 |
| gagagagtca | gaggggacaa | caaggagtat | gagtactcag | tggagtgcca | ggaggacagt | 600 |
| gcctgcccag | ctgctgagga | gagtctgccc | attgaggtca | tggtggatgc | cgttcacaag | 660 |
| ctcaagtatg | aaaactacac | cagcagcttc | ttcatcaggg | acatcatcaa | acctgaccca | 720 |
| cccaagaact | tgcagctgaa | gccattaaag | aattctcggc | aggtggaggt | cagctgggag | 780 |
| taccctgaca | cctggagtac | tccacattcc | tacttctccc | tgacattctg | cgttcaggtc | 840 |
| cagggcaaga | gcaagagaga | aaagaaagat | agagtcttca | cggacaagac | ctcagccacg | 900 |
| gtcatctgcc | gcaaaaatgc | cagcattagc | gtgcgggccc | aggaccgcta | ctatagctca | 960 |
| tcttggagcg | aatgggcatc | tgtgccctgc | agtcatcatc | accatcacca | ctga | 1014 |

<210> SEQ ID NO 4
<211> LENGTH: 337
<212> TYPE: PRT
<213> ORGANISM: Artificial Sequence
<220> FEATURE:
<223> OTHER INFORMATION: SP-hIL12p40 fusion polypeptide

<400> SEQUENCE: 4

Met Asp Pro Asp Asn Glu Ala Tyr Glu Met Pro Ser Glu Glu Gly Tyr
1               5                   10                  15

Gln Asp Tyr Glu Pro Glu Ala Gly Ser Ile Trp Glu Leu Lys Lys Asp
            20                  25                  30

Val Tyr Val Val Glu Leu Asp Trp Tyr Pro Asp Ala Pro Gly Glu Met
        35                  40                  45

Val Val Leu Thr Cys Asp Thr Pro Glu Glu Asp Gly Ile Thr Trp Thr
    50                  55                  60

Leu Asp Gln Ser Ser Glu Val Leu Gly Ser Gly Lys Thr Leu Thr Ile
65                  70                  75                  80

Gln Val Lys Glu Phe Gly Asp Ala Gly Gln Tyr Thr Cys His Lys Gly
                85                  90                  95

Gly Glu Val Leu Ser His Ser Leu Leu Leu Leu His Lys Lys Glu Asp
            100                 105                 110

Gly Ile Trp Ser Thr Asp Ile Leu Lys Asp Gln Lys Glu Pro Lys Asn
            115                 120                 125

Lys Thr Phe Leu Arg Cys Glu Ala Lys Asn Tyr Ser Gly Arg Phe Thr
130                 135                 140

Cys Trp Trp Leu Thr Thr Ile Ser Thr Asp Leu Thr Phe Ser Val Lys
145                 150                 155                 160

Ser Ser Arg Gly Ser Ser Asp Pro Gln Gly Val Thr Cys Gly Ala Ala
            165                 170                 175

Thr Leu Ser Ala Glu Arg Val Arg Gly Asp Asn Lys Glu Tyr Glu Tyr
            180                 185                 190

Ser Val Glu Cys Gln Glu Asp Ser Ala Cys Pro Ala Ala Glu Glu Ser
            195                 200                 205

Leu Pro Ile Glu Val Met Val Asp Ala Val His Lys Leu Lys Tyr Glu
            210                 215                 220

Asn Tyr Thr Ser Ser Phe Phe Ile Arg Asp Ile Ile Lys Pro Asp Pro
225                 230                 235                 240

Pro Lys Asn Leu Gln Leu Lys Pro Leu Lys Asn Ser Arg Gln Val Glu
            245                 250                 255

Val Ser Trp Glu Tyr Pro Asp Thr Trp Ser Thr Pro His Ser Tyr Phe
            260                 265                 270

Ser Leu Thr Phe Cys Val Gln Val Gln Gly Lys Ser Lys Arg Glu Lys
            275                 280                 285

Lys Asp Arg Val Phe Thr Asp Lys Thr Ser Ala Thr Val Ile Cys Arg
            290                 295                 300

Lys Asn Ala Ser Ile Ser Val Arg Ala Gln Asp Arg Tyr Tyr Ser Ser
305                 310                 315                 320

Ser Trp Ser Glu Trp Ala Ser Val Pro Cys Ser His His His His His
            325                 330                 335

His

<210> SEQ ID NO 5
<211> LENGTH: 687
<212> TYPE: DNA
<213> ORGANISM: Artificial Sequence
<220> FEATURE:
<223> OTHER INFORMATION: SP-hIL12p35 fusion coding sequence

<400> SEQUENCE: 5
atggaccctg acaatgaggc ttatgaaatg ccttctgagg aagggtatca agactacgaa     60
cctgaagccg gatccagaaa cctccccgtg gccactccag acccaggaat gttcccatgc    120
cttcaccact cccaaaacct gctgagggcc gtcagcaaca tgctccagaa ggccagacaa    180
actctagaat tttacccttg cacttctgaa gagattgatc atgaagatat cacaaaagat    240
aaaaccagca cagtggaggc ctgtttacca ttggaattaa ccaagaatga aagctgtctt    300
aactcaagag aaacttcatt tatcacaaac ggtagttgcc tggcctccag aaagacctct    360
tttatgatgg ccctgtgcct tagtagtatt tatgaagact gaagatgta ccaggtggag    420 ttcaagacca tgaatgcaaa gcttctgatg acccctaaga ggcaaatctt tctagatcaa    480
aacatgctgg cagttattga tgagctgatg caggccctga atttcaacag tgagactgtg    540
ccacaaaaat cctcccttga agaaccggat ttttataaaa ctaaaatcaa gctctgcata    600
cttcttcatg ctttcagaat tcgggcagtg actattgata gagtgatgag ctatctgaat    660
gcttcccatc atcaccatca ccactga                                       687

<210> SEQ ID NO 6
<211> LENGTH: 228
<212> TYPE: PRT
<213> ORGANISM: Artificial Sequence
<220> FEATURE:
<223> OTHER INFORMATION: SP-hIL12p35 fusion polypeptide

<400> SEQUENCE: 6

```
Met Asp Pro Asp Asn Glu Ala Tyr Glu Met Pro Ser Glu Glu Gly Tyr
1               5                   10                  15

Gln Asp Tyr Glu Pro Glu Ala Gly Ser Arg Asn Leu Pro Val Ala Thr
            20                  25                  30

Pro Asp Pro Gly Met Phe Pro Cys Leu His His Ser Gln Asn Leu Leu
        35                  40                  45

Arg Ala Val Ser Asn Met Leu Gln Lys Ala Arg Gln Thr Leu Glu Phe
    50                  55                  60

Tyr Pro Cys Thr Ser Glu Glu Ile Asp His Glu Asp Ile Thr Lys Asp
65                  70                  75                  80

Lys Thr Ser Thr Val Glu Ala Cys Leu Pro Leu Glu Leu Thr Lys Asn
                85                  90                  95

Glu Ser Cys Leu Asn Ser Arg Glu Thr Ser Phe Ile Thr Asn Gly Ser
            100                 105                 110

Cys Leu Ala Ser Arg Lys Thr Ser Phe Met Met Ala Leu Cys Leu Ser
        115                 120                 125

Ser Ile Tyr Glu Asp Leu Lys Met Tyr Gln Val Glu Phe Lys Thr Met
    130                 135                 140

Asn Ala Lys Leu Leu Met Asp Pro Lys Arg Gln Ile Phe Leu Asp Gln
145                 150                 155                 160

Asn Met Leu Ala Val Ile Asp Glu Leu Met Gln Ala Leu Asn Phe Asn
                165                 170                 175

Ser Glu Thr Val Pro Gln Lys Ser Ser Leu Glu Glu Pro Asp Phe Tyr
            180                 185                 190

Lys Thr Lys Ile Lys Leu Cys Ile Leu Leu His Ala Phe Arg Ile Arg
        195                 200                 205

Ala Val Thr Ile Asp Arg Val Met Ser Tyr Leu Asn Ala Ser His His
    210                 215                 220

His His His His
225
```

<210> SEQ ID NO 7
<211> LENGTH: 420
<212> TYPE: DNA
<213> ORGANISM: Artificial Sequence
<220> FEATURE:
<223> OTHER INFORMATION: hIL15-SP fusion coding sequence

<400> SEQUENCE: 7

```
atgaactggg tgaatgtaat aagtgatttg aaaaaaattg aagatcttat tcaatctatg      60
catattgatg ctactttata tacgaaaagt gatgttcacc ccagttgcaa agtaacagca     120
atgaagtgct ttctcttgga gttacaagtt atttcacttg agtccggaga tgcaagtatt     180
catgatacag tagaaaatct gatcatccta gcaaacaaca gtttgtcttc taatgggaat     240
gtaacagaat ctggatgcaa agaatgtgag gaactggagg aaaaaaatat taagaatttt     300
ttgcagagtt ttgtacatat tgtccaaatg ttcatcaaca cttctggatc cgatcctgac     360
aatgaggctt atgaaatgcc ttctgaggaa gggtatcaag actacgaacc tgaagcctaa     420
```

```
<210> SEQ ID NO 8
<211> LENGTH: 139
<212> TYPE: PRT
<213> ORGANISM: Artificial Sequence
<220> FEATURE:
<223> OTHER INFORMATION: hIL15-SP fusion polypeptide

<400> SEQUENCE: 8

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser Gly Ser Asp Pro Asp Asn Glu Ala Tyr Glu Met Pro Ser
        115                 120                 125

Glu Glu Gly Tyr Gln Asp Tyr Glu Pro Glu Ala
    130                 135

<210> SEQ ID NO 9
<211> LENGTH: 549
<212> TYPE: DNA
<213> ORGANISM: Artificial Sequence
<220> FEATURE:
<223> OTHER INFORMATION: SP-hIL18 fusion coding sequence

<400> SEQUENCE: 9
atggaccctg acaatgaggc ttatgaaatg ccttctgagg aagggtatca agactacgaa      60
cctgaagccg atcctactt tggcaagctt gaatctaaat tatcagtcat aagaaatttg     120
aatgaccaag ttctcttcat tgaccaagga atcggcctc tatttgaaga tatgactgat     180
tctgactgta gagataatgc accccggacc atatttatta agtatgta taaagatagc     240 cagcctagag gtatggctgt aactatctct gtgaagtgtg agaaaatttc aactctctcc     300
tgtgagaaca aaattatttc ctttaaggaa atgaatcctc tgataacat caaggataca     360 aaaagtgaca tcatattctt tcagagaagt gtcccaggac atgataataa gatgcaattt     420
gaatcttcat catacgaagg atactttcta gcttgtgaaa agagagaga ccttttaaa     480 ctcattttga aaaagagga tgaattgggg atagatcta taatgttcac tgttcaaaac     540
gaagactag                                                           549

<210> SEQ ID NO 10
<211> LENGTH: 182
<212> TYPE: PRT
<213> ORGANISM: Artificial Sequence
<220> FEATURE:
<223> OTHER INFORMATION: SP-hIL18 fusion polypeptide

<400> SEQUENCE: 10

Met Asp Pro Asp Asn Glu Ala Tyr Glu Met Pro Ser Glu Glu Gly Tyr
1               5                   10                  15
```

```
                Gln Asp Tyr Glu Pro Glu Ala Gly Ser Tyr Phe Gly Lys Leu Glu Ser
                             20                  25                  30

Lys Leu Ser Val Ile Arg Asn Leu Asn Asp Gln Val Leu Phe Ile Asp
                         35                  40                  45

Gln Gly Asn Arg Pro Leu Phe Glu Asp Met Thr Asp Ser Asp Cys Arg
                     50                  55                  60

Asp Asn Ala Pro Arg Thr Ile Phe Ile Ile Ser Met Tyr Lys Asp Ser
                 65                  70                  75                  80

Gln Pro Arg Gly Met Ala Val Thr Ile Ser Val Lys Cys Glu Lys Ile
                                 85                  90                  95

Ser Thr Leu Ser Cys Glu Asn Lys Ile Ile Ser Phe Lys Glu Met Asn
                            100                 105                 110

Pro Pro Asp Asn Ile Lys Asp Thr Lys Ser Asp Ile Ile Phe Phe Gln
                        115                 120                 125

Arg Ser Val Pro Gly His Asp Asn Lys Met Gln Phe Glu Ser Ser Ser
                    130                 135                 140

Tyr Glu Gly Tyr Phe Leu Ala Cys Glu Lys Glu Arg Asp Leu Phe Lys
                145                 150                 155                 160

Leu Ile Leu Lys Lys Glu Asp Glu Leu Gly Asp Arg Ser Ile Met Phe
                                165                 170                 175

Thr Val Gln Asn Glu Asp
                            180

<210> SEQ ID NO 11
<211> LENGTH: 24
<212> TYPE: DNA
<213> ORGANISM: Artificial Sequence
<220> FEATURE:
<223> OTHER INFORMATION: IL2-22-BamH1 forward primer

<400> SEQUENCE: 11
acaggatccc ctacttcaag ttct                                              24

<210> SEQ ID NO 12
<211> LENGTH: 28
<212> TYPE: DNA
<213> ORGANISM: Artificial Sequence
<220> FEATURE:
<223> OTHER INFORMATION: IL2-153-Xho reverse primer

<400> SEQUENCE: 12
cactctcgag tcaagtcagt gttgagat                                          28

<210> SEQ ID NO 13
<211> LENGTH: 30
<212> TYPE: DNA
<213> ORGANISM: Artificial Sequence
<220> FEATURE:
<223> OTHER INFORMATION: IL12-p40-23-BamH1 forward primer

<400> SEQUENCE: 13
gtggatccat atgggaactg aagaaagatg                                        30

<210> SEQ ID NO 14
<211> LENGTH: 32
<212> TYPE: DNA
<213> ORGANISM: Artificial Sequence
<220> FEATURE:
<223> OTHER INFORMATION: IL12-p40-328-CT-His reverse primer

<400> SEQUENCE: 14
```
atggtgatga tgactgcagg gcacagatgc cc                          32

<210> SEQ ID NO 15
<211> LENGTH: 25
<212> TYPE: DNA
<213> ORGANISM: Artificial Sequence
<220> FEATURE:
<223> OTHER INFORMATION: IL12-p35-23-BamH1 forward primer

<400> SEQUENCE: 15
gtggatccag aaacctcccc gtggc                                  25

<210> SEQ ID NO 16
<211> LENGTH: 29
<212> TYPE: DNA
<213> ORGANISM: Artificial Sequence
<220> FEATURE:
<223> OTHER INFORMATION: IL12-p35-219-CT-His reverse primer

<400> SEQUENCE: 16
atggtgatga tgggaagcat tcagatagc                              29

<210> SEQ ID NO 17
<211> LENGTH: 30
<212> TYPE: DNA
<213> ORGANISM: Artificial Sequence
<220> FEATURE:
<223> OTHER INFORMATION: IL15-49-Nde forward primer

<400> SEQUENCE: 17
gagtcaagca tatgaactgg gtgaatgtaa                             30

<210> SEQ ID NO 18
<211> LENGTH: 24
<212> TYPE: DNA
<213> ORGANISM: Artificial Sequence
<220> FEATURE:
<223> OTHER INFORMATION: IL15-162-BamH1 reverse primer

<400> SEQUENCE: 18
gtggatccag aagtgttgat gaac                                   24

<210> SEQ ID NO 19
<211> LENGTH: 24
<212> TYPE: DNA
<213> ORGANISM: Artificial Sequence
<220> FEATURE:
<223> OTHER INFORMATION: IL18-37-BamH1 forward primer

<400> SEQUENCE: 19
gtggatccta ctttggcaag cttg                                   24

<210> SEQ ID NO 20
<211> LENGTH: 27
<212> TYPE: DNA
<213> ORGANISM: Artificial Sequence
<220> FEATURE:
<223> OTHER INFORMATION: IL18-193-EcoR1 reverse primer

<400> SEQUENCE: 20
agactggaat tcctagtctt cgttttg                                27

<210> SEQ ID NO 21
<211> LENGTH: 140
<212> TYPE: PRT
<213> ORGANISM: Homo Sapien

```
<220> FEATURE:
<223> OTHER INFORMATION: human alpha synuclein

<400> SEQUENCE: 21

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 22
<211> LENGTH: 13
<212> TYPE: PRT
<213> ORGANISM: Homo Sapien
<220> FEATURE:
<223> OTHER INFORMATION: human alpha synuclein / C-terminal acidic tail
      domain residues 103-115

<400> SEQUENCE: 22

Asn Glu Glu Gly Ala Pro Gln Glu Gly Ile Leu Glu Asp
1               5                   10

<210> SEQ ID NO 23
<211> LENGTH: 23
<212> TYPE: PRT
<213> ORGANISM: Homo Sapien
<220> FEATURE:
<223> OTHER INFORMATION: human alpha synuclein / C-terminal acidic tail
      domain residues 114-126

<400> SEQUENCE: 23

Glu Glu Gly Ala Pro Gln Glu Gly Ile Leu Glu Asp Met Pro Val Asp
1               5                   10                  15

Pro Asp Asn Glu Ala Tyr Glu
            20

<210> SEQ ID NO 24
<211> LENGTH: 22
<212> TYPE: PRT
<213> ORGANISM: Homo Sapien
<220> FEATURE:
<223> OTHER INFORMATION: human alpha synuclein / C-terminal acidic tail
      domain residues 119-140

<400> SEQUENCE: 24

Asp Pro Asp Asn Glu Ala Tyr Glu Met Pro Ser Glu Glu Gly Tyr Gln
1               5                   10                  15

Asp Tyr Glu Pro Glu Ala
            20
```

<210> SEQ ID NO 25
<211> LENGTH: 11
<212> TYPE: PRT
<213> ORGANISM: Homo Sapien
<220> FEATURE:
<223> OTHER INFORMATION: human alpha synuclein / C-terminal acidic tail
    domain residues 130-140

<400> SEQUENCE: 25

```
Glu Glu Gly Tyr Gln Asp Tyr Glu Pro Glu Ala
1               5                   10
```

<210> SEQ ID NO 26
<211> LENGTH: 134
<212> TYPE: PRT
<213> ORGANISM: Homo Sapien
<220> FEATURE:
<223> OTHER INFORMATION: human beta synuclein

<400> SEQUENCE: 26

```
Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45

Val Gln Gly Val Ala Ser Val Ala Glu Lys Thr Lys Glu Gln Ala Ser
    50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95

Glu Val Ala Gln Glu Ala Ala Glu Glu Pro Leu Ile Glu Pro Leu Met
            100                 105                 110

Glu Pro Glu Gly Glu Ser Tyr Glu Asp Pro Pro Gln Glu Glu Tyr Gln
        115                 120                 125

Glu Tyr Glu Pro Glu Ala
    130
```

<210> SEQ ID NO 27
<211> LENGTH: 50
<212> TYPE: PRT
<213> ORGANISM: Homo Sapien
<220> FEATURE:
<223> OTHER INFORMATION: human beta synuclein / C-terminal acidic tail
    domain residues 85-134

<400> SEQUENCE: 27

```
Lys Arg Glu Glu Phe Pro Thr Asp Leu Lys Pro Glu Glu Val Ala Gln
1               5                   10                  15

Glu Ala Ala Glu Glu Pro Leu Ile Glu Pro Leu Met Glu Pro Glu Gly
            20                  25                  30

Glu Ser Tyr Glu Asp Pro Pro Gln Glu Glu Tyr Gln Glu Tyr Glu Pro
        35                  40                  45

Glu Ala
    50
```

<210> SEQ ID NO 28
<211> LENGTH: 127
<212> TYPE: PRT

```
<213> ORGANISM: Homo Sapien
<220> FEATURE:
<223> OTHER INFORMATION: human gamma synuclein (synoretin)

<400> SEQUENCE: 28

Met Asp Val Phe Lys Lys Gly Phe Ser Ile Ala Lys Glu Gly Val Val
1               5                   10                  15

Gly Ala Val Glu Lys Thr Lys Gln Gly Val Thr Glu Ala Ala Glu Lys
                20                  25                  30

Thr Lys Glu Gly Val Met Tyr Val Gly Ala Lys Thr Lys Glu Asn Val
            35                  40                  45

Val Gln Ser Val Thr Ser Val Ala Glu Lys Thr Lys Glu Gln Ala Asn
        50                  55                  60

Ala Val Ser Glu Ala Val Val Ser Ser Val Asn Thr Val Ala Thr Lys
65                  70                  75                  80

Thr Val Glu Glu Ala Glu Asn Ile Ala Val Thr Ser Gly Val Val Arg
                85                  90                  95

Lys Glu Asp Leu Arg Pro Ser Ala Pro Gln Gln Glu Gly Glu Ala Ser
            100                 105                 110

Lys Glu Lys Glu Glu Val Ala Glu Glu Ala Gln Ser Gly Gly Asp
        115                 120                 125

<210> SEQ ID NO 29
<211> LENGTH: 32
<212> TYPE: PRT
<213> ORGANISM: Homo Sapien
<220> FEATURE:
<223> OTHER INFORMATION: human gamma synuclein (synoretin) / C-terminal
      acidic tail domain residues 96-127

<400> SEQUENCE: 29

Arg Lys Glu Asp Leu Arg Pro Ser Ala Pro Gln Gln Glu Gly Glu Ala
1               5                   10                  15

Ser Lys Glu Lys Glu Glu Val Ala Glu Glu Ala Gln Ser Gly Gly Asp
                20                  25                  30
```